(12) United States Patent
Homan et al.

(10) Patent No.: US 11,340,375 B2
(45) Date of Patent: May 24, 2022

(54) MULTI-FREQUENCY ELECTROMAGNETIC TENSOR MEASUREMENTS

(71) Applicant: Schlumberger Technology Corporation, Sugar Land, TX (US)

(72) Inventors: Dean M. Homan, Sugar Land, TX (US); John Rasmus, Richmond, TX (US); Siddharth Misra, Austin, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 682 days.

(21) Appl. No.: 16/120,843

(22) Filed: Sep. 4, 2018

(65) Prior Publication Data
US 2018/0372905 A1    Dec. 27, 2018

Related U.S. Application Data

(62) Division of application No. 14/827,632, filed on Aug. 17, 2015, now Pat. No. 10,067,257.
(Continued)

(51) Int. Cl.
*G01V 3/12* (2006.01)
*G01V 3/28* (2006.01)
(Continued)

(52) U.S. Cl.
CPC ............. *G01V 3/12* (2013.01); *G01N 33/24* (2013.01); *G01V 3/28* (2013.01); *G01V 3/30* (2013.01); *G01V 3/38* (2013.01)

(58) Field of Classification Search
CPC ... G01V 3/12; G01V 3/28; G01V 3/30; G01V 3/38; G01N 33/24
See application file for complete search history.

(56) References Cited

U.S. PATENT DOCUMENTS 4,490,676 A * 12/1984 Davis, Jr. ............. G01N 33/241
                                                                324/376
4,686,477 A *  8/1987 Givens .................... G01V 3/24
                                                                324/366
(Continued)

FOREIGN PATENT DOCUMENTS

EP         2237075 A1   10/2010
WO   WO2014003784 A2    1/2014

OTHER PUBLICATIONS

International Search Report and Written Opinion issued in International Patent application PCT/US2015/045611 dated Dec. 30, 2015, 16 pages.
(Continued)

*Primary Examiner* — Kamini S Shah
*Assistant Examiner* — Peter Pham
(74) *Attorney, Agent, or Firm* — Jeffrey D. Frantz

(57) ABSTRACT

An electromagnetic measurement tool for making multi-frequency, full tensor, complex, electromagnetic measurements includes a triaxial transmitter and a triaxial receiver deployed on a tubular member. An electronic module is configured to obtain electromagnetic measurements at four or more distinct frequencies. The measurement tool may be used for various applications including obtaining a resistivity of sand layers in an alternating shale-sand formation; computing a dielectric permittivity, a conductivity anisotropy, and/or a permittivity anisotropy of a formation sample; and/or identifying formation mineralization including discriminating between pyrite and graphite inclusions and/or computing weight percent graphite and/or pyrite in the formation sample.

9 Claims, 14 Drawing Sheets

Related U.S. Application Data

(60) Provisional application No. 62/038,765, filed on Aug. 18, 2014.

(51) Int. Cl.
  *G01N 33/24* (2006.01)
  *G01V 3/30* (2006.01)
  *G01V 3/38* (2006.01)

(56) References Cited

U.S. PATENT DOCUMENTS

| | | |
|---|---|---|
| 7,733,093 B2 | 6/2010 | Homan et al. |
| 2003/0057950 A1 | 3/2003 | Gao et al. |
| 2008/0066534 A1 | 3/2008 | Reid et al. |
| 2008/0290874 A1* | 11/2008 | Seleznev .................. G01V 3/12 324/337 |
| 2009/0242196 A1 | 10/2009 | Pao |
| 2009/0248309 A1 | 10/2009 | Neville et al. |
| 2009/0287416 A1* | 11/2009 | Minh ..................... G01V 11/00 702/7 |
| 2010/0258265 A1* | 10/2010 | Karanikas ............... E21B 36/04 165/45 |
| 2011/0074427 A1 | 3/2011 | Wang et al. |
| 2011/0238312 A1 | 9/2011 | Seydoux et al. |
| 2012/0001629 A1 | 1/2012 | Hopper et al. |
| 2014/0107928 A1* | 4/2014 | Roy ......................... G01V 3/32 702/7 |
| 2014/0209392 A1* | 7/2014 | Jamison ............... C04B 20/1033 175/217 |
| 2014/0225607 A1 | 8/2014 | Edwards et al. |
| 2015/0153474 A1* | 6/2015 | Donderici ................ G01V 3/38 324/339 |
| 2016/0187521 A1 | 6/2016 | Homan et al. |
| 2016/0282503 A1* | 9/2016 | Hou ........................ G01V 3/28 |

OTHER PUBLICATIONS

International Preliminary Report on Patentability issued in International Patent application PCT/US2015/045611 dated Mar. 2, 2017, 15 pages.

* cited by examiner

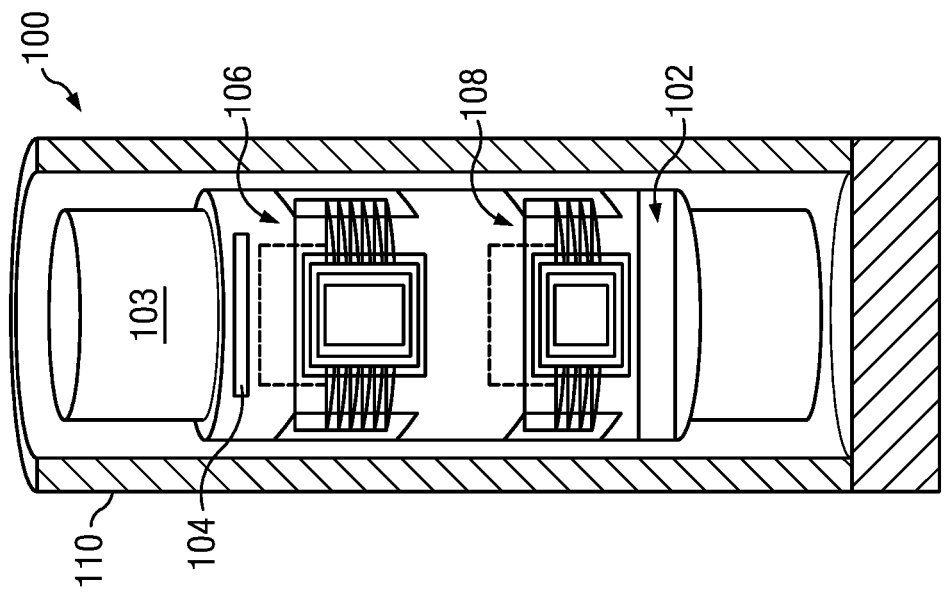
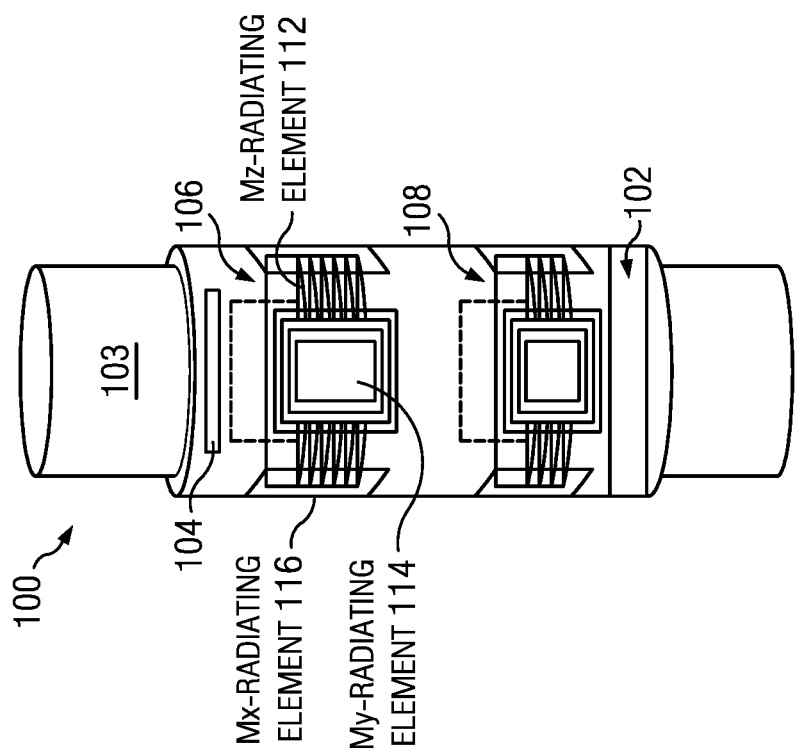

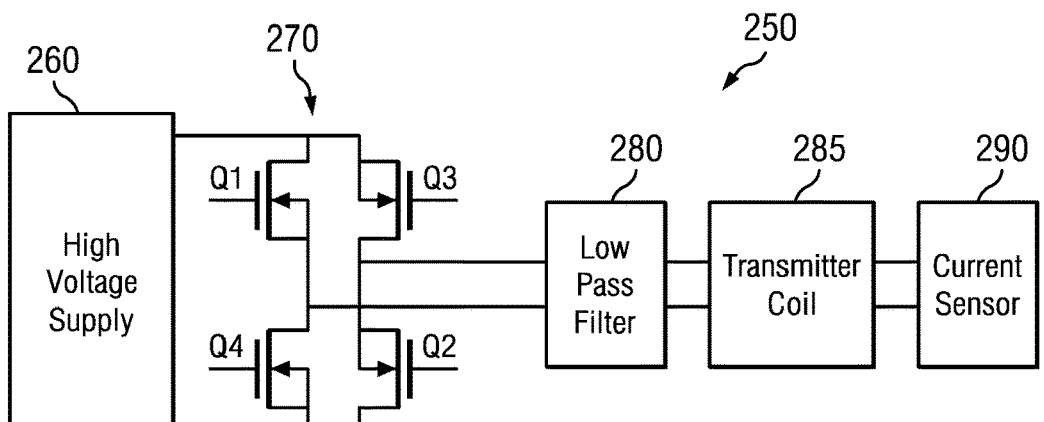
*FIG. 4*
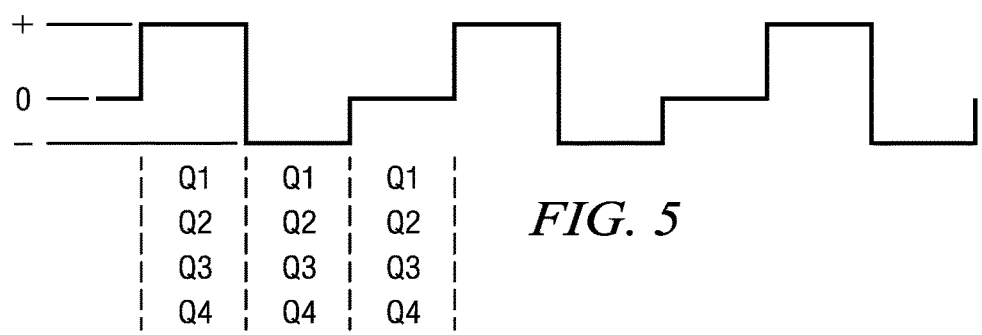
*FIG. 5*
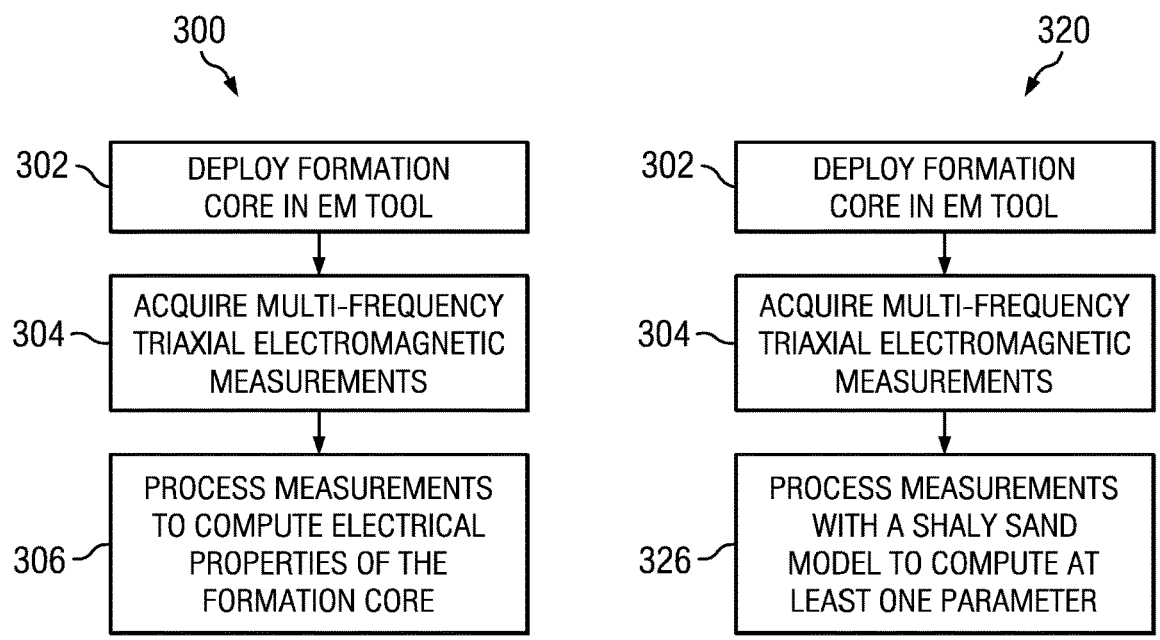
*FIG. 6A*  *FIG. 6B*

MULTI-FREQUENCY ELECTROMAGNETIC TENSOR MEASUREMENTS

CROSS REFERENCE TO RELATED APPLICATIONS

This application claims the benefit of U.S. Provisional Application Ser. No. 62/038,765 entitled Multi Frequency Complex Conductivity Tensor Measurements for Accurate Hydrocarbon Estimation in Formation Exhibiting Conductivity or Dielectric Dispersion, filed Aug. 18, 2014. This application is also a divisional of U.S. Non-provisional application Ser. No. 14/827,632 entitled Multi-Frequency Electromagnetic Tensor Measurements.

FIELD OF THE INVENTION

Disclosed embodiments relate generally to electromagnetic logging methods and more particularly to a logging tool and methods for making multi-frequency electromagnetic tensor measurements.

BACKGROUND INFORMATION

The use of electromagnetic measurements in prior art downhole applications, such as logging while drilling (LWD) and wireline logging applications is well known. Such techniques may be utilized to determine a subterranean formation resistivity, which, along with formation porosity measurements, is often used to indicate the presence of hydrocarbons in the formation. Moreover, azimuthally sensitive directional resistivity measurements are commonly employed e.g., in pay-zone steering applications, to provide information upon which steering decisions may be made.

Conventional interpretations of electromagnetic measurements neglect effects from dielectric permittivity, dielectric permittivity anisotropy, dielectric loss factor, permeability, and interfacial polarization phenomena (e.g., in an anisotropic medium). Such conventional interpretations, by their very nature, tend to assume that the electric field in the formation due to an EM source in the borehole is not affected, for example, by the interfacial polarization of clay minerals, clay-sized particles, and conductive minerals.

However, exploration and production in geologically complex reservoirs, such as shaly sands, sand-shale laminations, and organic-rich mudrocks, has become common. Moreover, electromagnetic measurements in these formations may exhibit directional and frequency dispersive characteristics due to the effects of electrical conductivity anisotropy, dielectric permittivity anisotropy, and interfacial polarization phenomena. Therefore, a need remains account for the effects of these parameters when making electromagnetic measurements of geological formations.

SUMMARY

An electromagnetic measurement tool for making electromagnetic measurements on a formation sample is disclosed. The tool includes a nonconductive tubular member configured to receive the formation sample. A triaxial transmitter and a triaxial receiver are deployed on the tubular member with the triaxial receiver being spaced apart from the triaxial transmitter along a longitudinal axis of the tubular member. An electronic module is configured to (i) cause the triaxial transmitter to transmit electromagnetic energy into the formation sample at four or more distinct and sequential frequencies and to (ii) cause the triaxial receiver to receive said transmitted electromagnetic energy each of the four or more frequencies.

Methods are disclosed for making multi-frequency electromagnetic measurements of a formation sample. In one method multi-frequency electromagnetic measurements are processed in combination with a formation model to compute at least one parameter of the formation model. For example, the measurements may be processed in combination with a shaly-sand model to obtain a resistivity of sand layers in the formation sample. In another method real and imaginary components of multi-frequency electromagnetic measurements may be processed to compute at least a dielectric permittivity, a conductivity anisotropy, or a permittivity anisotropy of the formation sample. For example, these parameters may be computed at a plurality of distinct measurement frequencies. In still another real and imaginary components of multi-frequency electromagnetic measurements may be processed to identify formation mineralization, for example, to discriminate between pyrite and graphite inclusions and/or to compute weight percent graphite and/or pyrite in the formation sample.

The disclosed embodiments may provide various technical advantages. For example, the disclosed methodology provides a measurement tool for making multi-frequency, full tensor, complex conductivity measurements of a formation sample such as a formation core. Such measurements may be utilized for a number of applications, for example, including obtaining a resistivity of a sand layer in a formation having alternating sand shale layers; computing frequency dispersive parameters of a formation sample such as a complex dielectric permittivity, a conductivity anisotropy, and/or dielectric permittivity anisotropy; and identifying formation mineralization including pyrite and graphite inclusions.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

For a more complete understanding of the disclosed subject matter, and advantages thereof, reference is now made to the following descriptions taken in conjunction with the accompanying drawings, in which:

FIGS. 1A and 1B depict example embodiments of disclosed electromagnetic measurement tools.

FIG. 4 depicts a transmitter waveform generator that may be used in the resonance circuit shown on FIG. 3.

FIG. 5 depicts an example waveform generated by the waveform generator shown on FIG. 4.

FIGS. 6A and 6B depict flow charts of disclosed method embodiments for making multi-frequency, complex conductivity triaxial tensor measurements.

DETAILED DESCRIPTION

Figure 2:
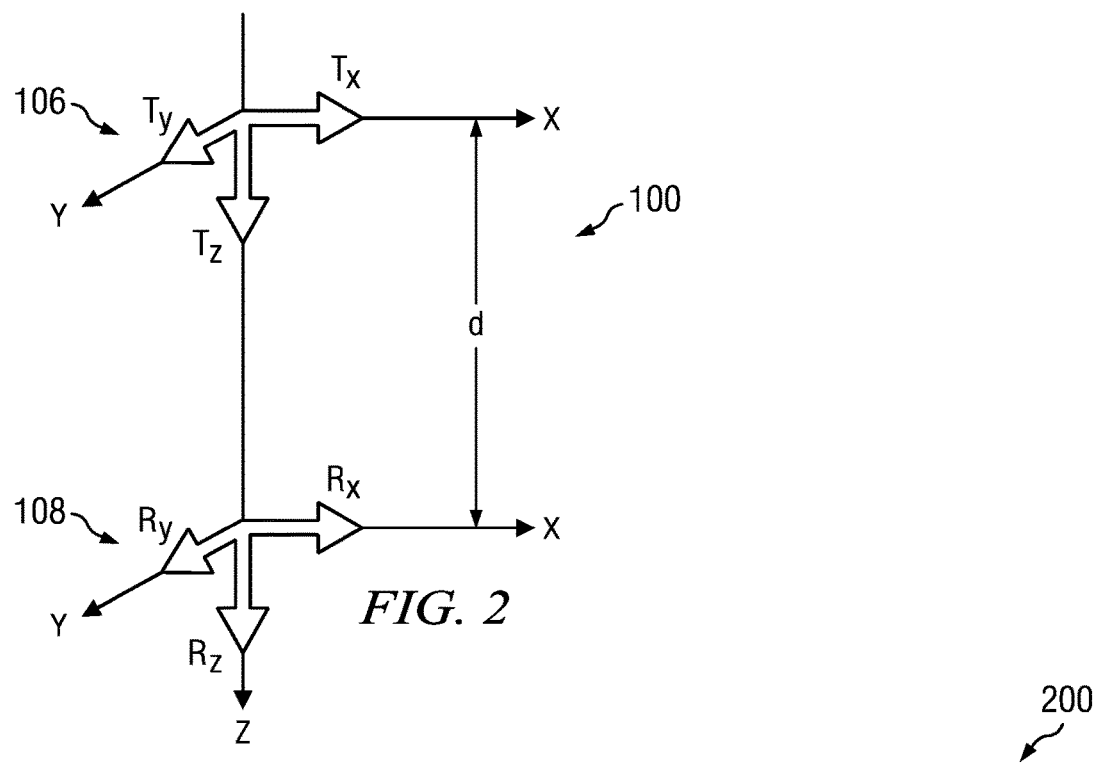
FIG. 2 depicts the magnetic moments (magnetic dipoles) of the tool embodiments depicted on FIGS. 1A and 1B.

FIG. 1A depicts one example of an electromagnetic measurement tool 100 (e.g., a triaxial induction tool). The depicted embodiment includes a tube 102 on which at least one triaxial array, including a triaxial transmitter 106 and a triaxial receiver 108, is deployed. The tube 102 is configured (e.g., sized and shaped) to receive a formation core 103 and may be fabricated from substantially any non-conductive material such as, for example, fiberglass. Measurement tool 100 may further include an electronics module 104 configured to energize the triaxial transmitter 106 and for controlling the acquisition of the electromagnetic wave (voltages) by triaxial receiver 108. The module 104 may further include a processor and/or a memory for executing and storing a program for performing data processing.

As stated above, measurement tool 100 includes a triaxial transmitter 106 and a triaxial receiver 108 deployed on tube 102. In the depicted embodiment, the triaxial transmitter includes three radiating elements 112, 114, and 116 (e.g., three transmitting antennas) arranged in a (x, y, z) coordinate system. The triaxial receiver also includes three corresponding receiving antennas arranged in a (x, y, z) coordinate system. For example, each of transmitter 106 and receiver 108 may include a triaxial antenna arrangement including an axial antenna and first and second transverse antennas that are orthogonal to one another. By axial it is meant that the antenna moment is substantially parallel with the longitudinal axis of the tube 102. In such an embodiment, an axial antenna may be wound about the circumference of the tube 102 such that the plane of the antenna is substantially orthogonal to the tube axis. By transverse it is meant that the antenna moment is substantially orthogonal to the longitudinal axis of the tube 102. A transverse antenna may include, for example, a saddle coil (e.g., as disclosed in U.S. Patent Publications 2011/0074427 and 2011/0238312 each of which is incorporated by reference herein).

FIG. 1B depicts another example of the measurement tool 100 shown in FIG. 1A. In this embodiment, the measurement tool 100 is deployed in a cylindrical housing 110 such as logging sonde or a logging while drilling tool body. The cylindrical housing may be made of any conductive, non-magnetic material such as, for example, copper, brass, aluminum, a non-magnetic steel such as stainless steel, or the like. It will be understood that measurement tool 100 may be employed in evaluating the electromagnetic properties of a formation core obtained, for example, in an axial coring operation or a sidewall coring operation. The measurement tool 100 may therefore be deployed in a downhole tool such as a wireline logging and/or coring tool, a logging while drilling tool, or a coring while drilling tool. The measurement tool 100 may also be deployed at the surface, for example, in a formation evaluation laboratory.

In embodiments suitable for making formation core measurements, the tube 102 may be sized and shaped to receive a formation core, having a diameter of about four inches. Moreover, the axial distance d between the triaxial transmitter 106 and the triaxial receiver 108 may be in the range from about 3 to about 6 inches (although the disclosed embodiments are by no means limited in this regard). U.S. Pat. No. 7,733,093, which is fully incorporated by reference herein, discloses one measurement tool configuration for making electromagnetic measurements of a formation core.

FIG. 2 depicts the magnetic moments (magnetic dipoles) of the embodiments depicted on FIGS. 1A and 1B. The triaxial transmitter 106 includes three radiating elements (transmitting antenna) having magnetic dipoles $T_x$, $T_y$, and $T_z$ oriented in orthogonal directions (along x-, y-, and z-axes as depicted). The triaxial receiver 108 likewise includes three radiating elements (receiving antenna) having magnetic dipoles $R_x$, $R_y$, and $R_z$ oriented along the same orthogonal directions (the x-, y-, and z-axes). In the depicted embodiment, the z-axis is arbitrarily selected to be along the longitudinal axis of the tube 102, while the x-axis and y-axis are mutually perpendicular directions lying in the plane transverse to the tube axis (the z-axis). Although co-located transmitting and receiving antenna are depicted, it will be understood that such a configuration is not required. By co-located it is meant that the centers of the radiating elements are substantially at the same location.

With continued reference to FIGS. 1A, 1B, and 2, the electronics module 104 may be configured to make a plurality of electromagnetic measurements at a corresponding plurality of discrete frequencies (within a predetermined range of frequencies). For example, the electronics module 104 may be configured to cause the triaxial transmitter to radiate an electromagnetic wave at a first frequency and cause the triaxial receiver to measure the corresponding electromagnetic waves (voltages). The electronics module 104 may then cause the triaxial transmitter to radiate an electromagnetic wave at a second frequency and cause the triaxial receiver to measure the corresponding electromagnetic waves at the second frequency. The electronics module 104 is configured to continue this frequency "scan" until electromagnetic measurements have been made at each of the predetermined frequencies. Such a measurement protocol may be thought of as being spectroscopic in that it involves making electromagnetic measurements as a function of the excitation frequency (over a predetermined range of frequencies). The electromagnetic measurements may be made over substantially any frequency range and may include substantially any number of frequencies, e.g., in a frequency range from about 1 kHz to about 10 MHz (e.g., from about 1 kHz to about 2 MHz, from about 1 kHz to about 500 kHz, or from about 5 to about 500 kHz) including 4 or more (e.g., 6 or more, 8 or more, 10 or more, or 12 or more) discrete frequencies. For example, in one non-limiting embodiment the frequencies may include 10, 20, 30, 40, 60, 90, 150, and 260 kHz.

The triaxial transmitting antennas (i.e., the x-axis, y-axis, and z-axis antennas) may be configured such that the natural frequency of the antenna is greater than the highest frequency measurement among the predetermined frequencies (e.g., greater than 10 MHz). This may be accomplished, for example, via managing the inductance and resistance of the antennas (e.g., based on the known material properties of the antennas) or via configuring the electronics circuit with negative capacitance feedback.

Upon selecting the appropriate drive frequencies the transmitting antennas may be driven at a resonance for each of the desired frequencies by switching a resonance capacitor in series with or parallel to the transmitting antennas. Driving the transmitting antennas at resonance advantageously minimizes the antenna impedance and thereby maximizes the current driven through the antenna (which in turn maximizes the intensity of the transmitted electromagnetic wave). This results in a larger current in the formation and ultimately a larger voltage on the triaxial receivers. The receivers may be configured to terminate into a high impedance broadband amplifier followed by a notch filter configured to notch at the multiple drive frequencies. While FIGS. 1 and 2 depict a single spacing core analysis tool embodiment, it will be understood that the above described measurement tool configured for making triaxial, multi-frequency electromagnetic measurements may also be readily extended to making multi-spacing measurements (e.g., utilizing multiple spaced triaxial transmitters and/or multiple spaced triaxial receivers) for wireline and/or logging while drilling operations in which the electromagnetic properties of the subterranean formation (rather than a formation core) are evaluated.

Figure 3:
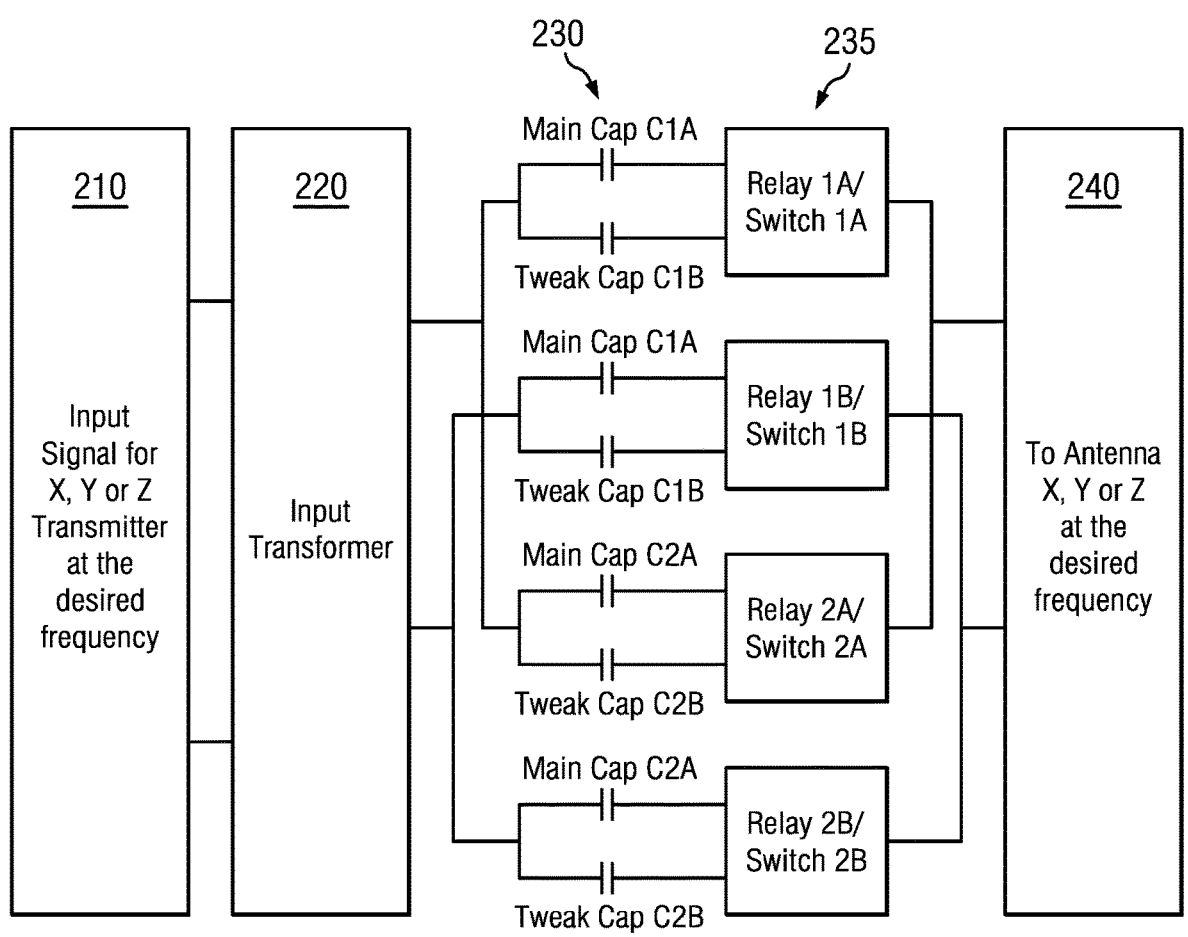
FIG. 3 depicts one example of a transmitter resonance circuit/block diagram for use in the measurement tools depicted on FIGS. 1A and 1B.

Turning now to FIG. 3, one example of a transmitter resonance circuit/block diagram 200 is depicted. The example circuit may be deployed in electronics module 104 and combines the x-axis, y-axis, and z-axis transmitting antenna circuitry on a single board enclosed in a common housing (e.g., a metal box). The resonance circuits are designed to maximize the current that is driven through the real impedance of the coil and to consequently minimize the current flowing through the parallel capacitance of the cabling and the coil. An input signal is generated using frequency generator 210 including, for example, lock-in amplifier or a signal generator. An input transformer 220 receives the input signal and steps up the signal, for example, to provide impedance matching with the antenna. The signal may then be passed through a parallel capacitive bank 230 including a relay or switch 235 to select the predetermined frequency. The signal may then be applied to the transmitting antenna 240 to generate a corresponding electromagnetic wave.

With continued reference to FIG. 3, it will be understood that the depicted embodiment is schematic in nature and highly simplified for ease of illustration. As depicted, the resonance circuit 200 is configured to provide a single frequency to the x-, y-, and z-axis transmitting antennas. The signal is provided to the z-axis transmitting antenna via switches 1A and 2A (which may be opened simultaneously). Corresponding capacitors C1A and C1B in capacitor bank 230 (and connected to switch 1A) provide resonance at the predetermined frequency. Capacitors C2A and C2B (connected to switch 2A) are intended to cancel the inductance of the antenna. The signal is provided to the x- or y-axis transmitting antennas via switches 1B and 2B (which may be open simultaneously). Capacitors C1A and C1B in capacitor bank 230 (and connected to switch 1B) provide resonance at the predetermined frequency. Capacitors C2A and C2B (connected to switch 2B) are intended to cancel the inductance of the antenna. It will be understood that multiple sequential frequencies may be generated, for example, by providing additional capacitor banks in parallel with those depicted. Input signals may then be provided at the predetermined multiple frequencies by opening and closing the appropriate switches (or relays). These relay/switch sets 235 may be controlled by an external multiplexer unit (not depicted) which switches them based on the desired frequency signal at the input such that the output signal is routed to the appropriate antenna (x, y, or z) at the desired frequency.

Current flowing through the transmitter may optionally be measured via a pick-off transformer, a low drift resistor and an AD8228 (Low Gain Drift Precision Instrumentation Amplifier) within the transmitter resonance circuit by an external Agilent 34401A 6.5 digit multi-meter. These features are not depicted on FIG. 3.

The transmitter resonance circuit can also be implemented using a transmitter waveform generator 250, such as is schematically depicted on FIG. 4. The generator 250 may be used to produce the main drive signal for the transmitter coils and is intended to replace the input signal generator 210 in FIG. 3. Generator 250 includes a high voltage supply 260, an H-bridge 270 including transistors Q1, Q2, Q3, and Q4, a low pass filter 280, a transmitter coil 285 and a current sensor 290.

With continued reference to FIG. 4 and further reference to FIG. 5, a transmitter drive voltage may be generated by alternately connecting the transmitter coil (i) to the high voltage power supply with positive polarity, (ii) to the high voltage power supply with negative polarity, and (iii) to ground. A switching control circuit controls the transistors Q1, Q2, Q3 and Q4 to produce the three different connections mentioned above. A positive polarity connection may be made when Q1 and Q2 are off and Q3 and Q4 are on. A negative polarity connection may be made when Q1 and Q2 are on and Q3 and Q4 are off. A ground connection may be made when Q2 and Q4 are on and Q1 and Q3 are off. The low pass filter 280 is used to remove high frequency harmonics resulting from the switching action of the transistors. A balancing transformer may be used to reduce capacitive coupling from the transmitter signal and receiver signals. The disclosed electromagnetic measurement tool embodiments are, of course, not limited in regards to any of the switching and signal generation elements depicted on FIGS. 3-5.

FIG. 6A depicts a flow chart of one disclosed method embodiment 300 for making multi-frequency, complex conductivity tensor measurements of a subterranean formation core. The method includes deploying a substantially cylindrical formation core in an electromagnetic measurement tool at 302. For example, the formation core may be deployed in tube 102 of electromagnetic measurement tool 100 (FIG. 1). Triaxial electromagnetic measurements are acquired at 304, for example, by firing each of the x-axis, y-axis, and z-axis transmitting antennas and receiving corresponding electromagnetic waves (via voltage measurements) at the x-axis, y-axis, and z-axis receiving antennas to obtain a 3×3 voltage tensor. Such measurements are made acquired at 304 at plurality of distinct frequencies, each of the frequencies being in a range from about 1 kHz to about 10 MHz. For example, in one embodiment measurements are acquired at eight distinct frequencies in a range from about 5 kHz to about 500 kHz. The multi-frequency triaxial electromagnetic measurements may then be processed at 306 to compute formation properties such the conductivity, the conductivity anisotropy, the complex dielectric permittivity, and/or the dielectric permittivity anisotropy of the formation core. Such processing may include generating a cross-plot as described in more detail below with respect to FIGS. 7-9.

With continued reference to FIG. 6A, and as is known to those of ordinary skill in the art, a time varying electric current (an alternating current) in a transmitting antenna produces a corresponding time varying magnetic field in the local environment (e.g., in the formation core deployed in the tube of electromagnetic measurement tool 100). The magnetic field in turn induces electrical currents (eddy currents) in the conductive formation core. These eddy currents further produce secondary magnetic fields which may produce a voltage response in the receiving antennas. The measured voltage in the receiving antennas may then be processed to compute one or more properties of the formation.

In general earth formations are anisotropic such that the electrical and dielectric properties of a formation core may be expressed as three-dimensional tensors that contain information on formation resistivity anisotropy, permittivity anisotropy, dip, bed boundaries and other aspects of formation geometry. It will be understood by those of ordinary skill in the art that the mutual couplings between tri-axial transmitter antennas and tri-axial receiver antennas (e.g., as depicted on FIGS. 1A, 1B, and 2) form a three-dimensional matrix and thus may have sensitivity to a full three-dimensional formation impedance tensor. For example, a three-dimensional matrix of measured voltages V may be expressed as follows:

$$V = \begin{bmatrix} V_{xx} & V_{xy} & V_{xz} \\ V_{yx} & V_{yy} & V_{yz} \\ V_{zx} & V_{zy} & V_{zz} \end{bmatrix} = IZ = \begin{bmatrix} I_x & 0 & 0 \\ 0 & I_y & 0 \\ 0 & 0 & I_z \end{bmatrix} \begin{bmatrix} Z_{xx} & Z_{xy} & Z_{xz} \\ Z_{yx} & Z_{yy} & Z_{yz} \\ Z_{zx} & Z_{zy} & Z_{zz} \end{bmatrix} \quad (1)$$

where V represents the three-dimensional matrix of measured voltages I represents the transmitter currents in the x-y-, and z-axis transmitting antennas, and Z represents the transfer impedances which depend on the electrical, dielectric, and magnetic properties of the environment surrounding the antenna pair in addition to the frequency, geometry, and spacing of the antennas. The subscripts indicate the axial orientation of the transmitter and receiver antennas. For example, $V_{xy}$ represents a voltage measurement on the y-axis receiving antenna from a firing of the x-axis transmitting antenna.

Electromagnetic propagation may be described by Maxwell's equations. Ampere's law was extended by Maxwell to equate the curl of a magnetic field $\vec{\nabla} \times \vec{H}$ with the sum of the electrical current density $\vec{J}$ and the partial derivative in time of the electric flux density $\vec{D}$ and may be expressed as follows:

$$\vec{\nabla} \times \vec{H} = \vec{J} + \partial_t \vec{D} \quad (2)$$

Ohm's law equates the electrical current density $\vec{J}$ to the product of the electrical conductivity tensor $\overline{\sigma}$ and the applied electric field $\vec{E}$. Maxwell equates the electric flux density $\vec{D}$ (also sometimes referred to in the art as the displacement current) to the product of the dielectric permittivity tensor $\overline{\varepsilon}$ and the applied electric field $\vec{E}$ such that Equation 2 may be written as follows:

$$\vec{\nabla} \times \vec{H} = \overline{\sigma} \vec{E} - i\omega \overline{\varepsilon} \vec{E} \quad (3)$$

where a single induction measurement operates at a single circular frequency $\omega = 2\pi f$ with the explicit time dependence $e^{-i\omega t}$ such that $\partial_t(\overline{\varepsilon} \vec{E}) = -i\omega \overline{\varepsilon} \vec{E}$.

The dielectric permittivity $\overline{\varepsilon}$ and electric conductivity $\overline{\sigma}$ tensors may be combined into an effective complex-valued conductivity tensor $\overline{\sigma}'$ that takes into account charge migration and storage effects, for example, as follows:

$$\overline{\sigma}' = \overline{\sigma} - i\omega\overline{\varepsilon} = \overline{\sigma} - i\omega\varepsilon_o \overline{\varepsilon}_r = \overline{\tau} - i\sigma_o \overline{\varepsilon}_r \quad (4)$$

As given in Equation 4, the dielectric permittivity matrix $\overline{\varepsilon}$ is written as $\overline{\varepsilon} = \varepsilon_o \overline{\varepsilon}_r$ in which the dielectric permittivity matrix $\overline{\varepsilon}$ is a product of the absolute dielectric permittivity of vacuum ($\varepsilon_o \cong 8.8542 \times 10^{-12}$ As/m) and the relative dielectric permittivity $\overline{\varepsilon}_r$ matrix. The product of the angular frequency $\omega$ and the absolute vacuum permittivity $\varepsilon_o$ constitutes the conductivity $\sigma_o = \omega\varepsilon_o$ which is the "conductivity scale" that determines the weight of dielectric-permittivity effects on the electrical conductivity.

The effective complex-valued conductivity tensor $\overline{\sigma}'$ may be further express as a fully complex quantity, for example, as follows:

$$\overline{\sigma}' = \overline{\sigma}^* - i\omega\varepsilon_o \overline{\varepsilon}^* = \overline{\sigma}_{app} - i\omega\varepsilon_o \overline{\varepsilon}_{r,app} \quad (5)$$

where $\overline{\sigma}^*$ and $\overline{\varepsilon}^*$ represent full tensor, complex, frequency dependent quantities such that $\overline{\sigma}^*(\omega) = \overline{\sigma}(\omega) + i\overline{\sigma}(\omega)$ and $\bar{\varepsilon}^*(\omega)=\bar{\varepsilon}'(\omega)+i\bar{\varepsilon}''(\omega)$. For geo-materials (such as common earth formations), $\bar{\sigma}^*(\omega)$ may be assumed to be entirely real in the frequency range of interest such that $\bar{\sigma}^*(\omega)=\bar{\sigma}_{kHz}$. Substituting into Equation 5, yields the following expression:

$$\bar{\sigma}'=\bar{\sigma}_{kHz}+\omega\varepsilon_o\bar{\varepsilon}''(\omega)-i\omega\varepsilon_o\bar{\varepsilon}'(\omega) \quad (6)$$

Equations 3-6 describe the properties of an electromagnetic wave propagating through a medium having conductivity and a dielectric constant (or dielectric permittivity). Induction or propagation measurements are intended to measure the real and imaginary properties of this propagating wave. A propagation tool measures the attenuation and phase difference between two receiver antennas. By measuring these parameters at multiple frequencies and employing the constitutive equations given herein, the conductivity and dielectric constant of the medium may be computed. Such measurements may be valuable in certain formation types that have non-zero dielectric permittivity, for example, those including conductive elements such as pyrite, clay, or graphite dispersed in shale or formations having non-spherical conductive elements dispersed therein. The measurements described herein may then be useful to distinguish certain material properties of the dispersed elements. For example, the presence of pyrite and graphite (representing a mature kerogen) may be identified and quantified using the multi-frequency complex conductivity measurements. Since kerogen tends to become graphite with maturity, the measurements described herein may then further be interpreted to estimate the maturity of the kerogen. The following equations illustrate the methodology for a given oriented antenna pair.

The complex conductivity response of a multi-frequency electromagnetic measurement tool may be expressed mathematically, for example, as follows:

$$\sigma_{meas} = \text{Real}(\omega) + i\text{Imag}(\omega) = \frac{V_R(\omega)/I_T(\omega)}{K} \quad (7)$$

where $\sigma_{meas}$ represents the measured complex conductivity, $V_R$ represents the complex-valued voltage induced in the receiver coil, $I_T$ represents the current in the transmitter coil, and K represents the geometrical factor of transmitter-receiver coupling. It will be understood that $\sigma_{meas}$ is related to the complex formation properties via the wave number k.

Shale Sand Formation Models

FIG. 6B depicts a flow chart of another disclosed method embodiment 320 for making multi-frequency, complex conductivity tensor measurements of a subterranean formation core. The method 320 is similar to method 300 in that it includes deploying a substantially cylindrical formation core in an electromagnetic measurement tool at 302 and acquiring triaxial electromagnetic measurements at 304 at a plurality of distinct predetermined frequencies. The multi-frequency triaxial electromagnetic measurements may then be processed at 326 in combination with a shaly sand formation model to obtain at least one parameter value of the model. For example, the measurements may be processed to obtain a resistivity of the sand as described in more detail below. Such processing may include generating a cross-plot as described in more detail with respect to FIGS. 7-9.

As is known to those of ordinary skill in the art, geological formations commonly include deposited and buried stratigraphic layers having in-plane (in layer) and normal-to-plane properties (e.g., in plane and normal conductivities also sometimes referred to as horizontal and vertical conductivities or resistivities). Tensor resistivity measurements are intended to provide sufficient information to determine certain volumetric properties of the deposited beds that are below the resolution of the measurement tool, for example, including a horizontal resistivity $R_h$, vertical resistivity $R_v$, anisotropy ratio, dip and azimuth of the bed. It will be understood that resistivity and conductivity are reciprocal quantities such that $R=1/\sigma$ and are frequently used interchangeably herein.

A simplified shaly-sand model may be constructed, for example, as follows assuming zero dip in which the formation includes a thinly layered sequence of hydrocarbon filled sands and water saturated shales that are much thinner than the resolution of the measuring device. Such a formation may be represented by the following volumetric resistivity equations:

$$\frac{1}{R_h} = \frac{V_{shale}}{R_{shale}} + \frac{V_{sand}}{R_{sand}} \quad (8)$$

$$R_v = V_{shale}R_{shale} + V_{sand}R_{sand}$$

$$V_{shale} + V_{sand} = 1$$

where $R_{shale}$ and $R_{sand}$ represent the resistivity of the shale and sand layers, $V_{shale}$ and $V_{sand}$ represent the volume fractions of the shale and sand layers in the layered formation, and $R_h$ and $R_v$ represent the horizontal and vertical resistivity of the layered formation. $R_h$ and $R_v$ may be computed by inverting conventional triaxial (tensor) resistivity measurements leaving the volume fractions of shale and sand $V_{shale}$ and $V_{sand}$ and the resistivity of the shale and sand layers $R_{shale}$ and $R_{sand}$ as unknowns. $R_{sand}$ is commonly of particular importance to the geophysicist for use in computing water saturations of the sand layers. It will be understood that the resulting system is under-defined, having three equations and four unknowns, and therefore requires additional measurements. For example, $V_{shale}$ may be computed from a gamma ray log, a nuclear magnetic resonance (NMR) bound fluid volume computation, or a neutron-density separation. The remaining three unknowns $V_{sand}$, $R_{shale}$, and $R_{sand}$ may then be computed using Equation 8. Alternatively, $R_{shale}$ may be specified to be a constant thereby enabling $V_{sand}$, $V_{shale}$, and $R_{sand}$ to be computed in terms of $R_{shale}$.

The simplified model in Equation 8 may be extended to account for the observation that shale layers are commonly electrically anisotropic (having an anisotropy, for example, in a range from about 3 to about 10). Sand layers are commonly electrically isotropic. The modified model may then be expressed as follows:

$$\frac{1}{R_h} = \frac{V_{shale}}{R_{shale\_h}} + \frac{V_{sand}}{R_{sand}} \quad (9)$$

$$R_v = V_{shale}R_{shale\_v} + V_{sand}R_{sand}$$

$$V_{shale} + V_{sand} = 1$$

where $R_{shale\_h}$ and $R_{shale\_v}$ represent the horizontal and vertical resistivity of the shale layers in the layered formation. The remaining parameters are as defined above with respect to Equation 8. This set of equations is further undefined in that it now includes 5 unknowns and three equations. The introduction of the additional unknowns ($R_{shale\_h}$ and $R_{shale\_v}$) may be accounted for by identifying shale anisotropy of a representative shale layer, and using a butterfly cross-plot (as described in more detail below).

Those of skill in the art will appreciate that Archie's equation is a purely empirical equation intended to describe the flow of low frequency electrical current in clean, consolidated sands having varying intergranular porosity. Electrical conduction is assumed not to be present within the rock grains or in fluids other than water. Many believe that Archie's equation laid the foundation for modern well log interpretation as it relates borehole electrical conductivity measurements to hydrocarbon saturations for fluid saturated rock through the relation $S_{hc}=1-S_w$, where $S_w$ represents the water filled porosity in the sand and $S_{hc}$ represents the hydrocarbon filled porosity. Archie's equation is commonly expressed as follows:

$$S_w^n = \frac{a\sigma_t}{\phi^m \sigma_w} \quad (10)$$

where $\phi$ represents the formation porosity, m represents the cementation exponent of the rock (usually in the range 1.8-2.0 for shaly sands), n represents the saturation exponent (usually close to 2), n represents a tortuosity factor, and $\sigma_t$ and $\sigma_w$ represent the conductivity (inverse resistivity) of the formation and water respectively ($\sigma_t$ may also be thought of as being the conductivity of the sand in Equations 8 and 9 such that $\sigma_t = \sigma_{sand} = 1/R_{sand}$). A factor $F = a/\phi^m = R_o/R_w$ is referred to as a formation resistivity factor, where $R_o$ represents a resistivity of the rock filled only with conductive water and $R_w$ represents the resistivity of the water (i.e., with $S_w=1$). A factor $1 = R_t/R_o = S_w^{-n}$ is referred to as the resistivity index.

The shaly-sand volumetric models described above with respect to Equations 8 and 9 may be further extended to include shale layers that have both permittivity and conductivity (based on Equations 3-6). The further modified model may be expressed, for example, as follows:

$$\frac{1}{\sigma_v - i\sigma_o\varepsilon_v} = \frac{V_{shale}}{\sigma_{shale\_v} - i\sigma_o\varepsilon_{shale\_v}} + \frac{V_{sand}}{\sigma_{sand}} \quad (11)$$

$$\sigma_h - i\sigma_o\varepsilon_h = V_{shale}(\sigma_{shale\_h} - i\sigma_o\varepsilon_{shale\_h}) + V_{sand}\sigma_{sand}$$

$$V_{shale} + V_{sand} = 1$$

where $\sigma_v$ and $\sigma_h$ represent the vertical and horizontal conductivity of the layered formation, $\varepsilon_v$ and $\varepsilon_h$ represent the vertical and horizontal dielectric permittivity of the layered formation, or $\sigma_{shale)v}$ and $\sigma_{shale\_h}$ represent the vertical and horizontal conductivity of the shale layers, and $\varepsilon_{shale\_v}$ and $\varepsilon_{shale\_h}$ represent the vertical and horizontal dielectric permittivity of the shale layers. The remaining parameters are as defined above with respect to Equations 4, 8, and 9. It will be understood the Equation 11 is now explicitly frequency dependent since $\sigma_o = \omega\varepsilon_o$.

Rearranging Equation 11 into real and imaginary components yields the following relations:

$$\frac{\sigma_v}{\sigma_v^2 + \sigma_o^2\varepsilon_v^2} = \frac{V_{shale}\sigma_{shale\_v}}{\sigma_{shale\_v}^2 + \sigma_o^2\varepsilon_{shale\_v}^2} + \frac{V_{sand}}{\sigma_{sand}} \quad (12)$$

$$\frac{i\sigma_o\varepsilon_v}{\sigma_v^2 + \sigma_o^2\varepsilon_v^2} = \frac{V_{shale}i\sigma_o\varepsilon_{shale\_v}}{\sigma_{shale\_v}^2 + \sigma_o^2\varepsilon_{shale\_v}^2}$$

$$\sigma_h = V_{sand}\sigma_{sand} + V_{shale}\sigma_{shale\_h}$$

$$i\sigma_o\varepsilon_h = V_{shale}i\sigma_o\varepsilon_{shale\_h})$$

where the layered formation parameters $\sigma_v$, $\sigma_h$, $\varepsilon_v$, and $\varepsilon_h$ may be computed from the multi-frequency, full tensor electromagnetic measurements described above. Note also that in the limit of $\varepsilon_{shale\_v} \to 0$ and $\varepsilon_{shale\_h} \to 0$ Equation 12 reduces to Equation 9.

Archie's equation (Equation 10) may now be modified into a complex equation as follows:

$$S_w^n = \frac{a\sigma_t'}{\phi^m \sigma_w'} = \frac{a}{\phi^m}\frac{(\sigma_t - i\sigma_o\varepsilon_t)}{(\sigma_w - i\sigma_o\varepsilon_w)} \quad (13)$$

where $\varepsilon_t$ and $\varepsilon_w$ represent the dielectric permittivity of the formation and water respectively. It will be understood that other known water saturation equations may similarly be transformed into a complex formulation for use in the estimation of water saturation from complex conductivity tensor measurements.

Figure 7:
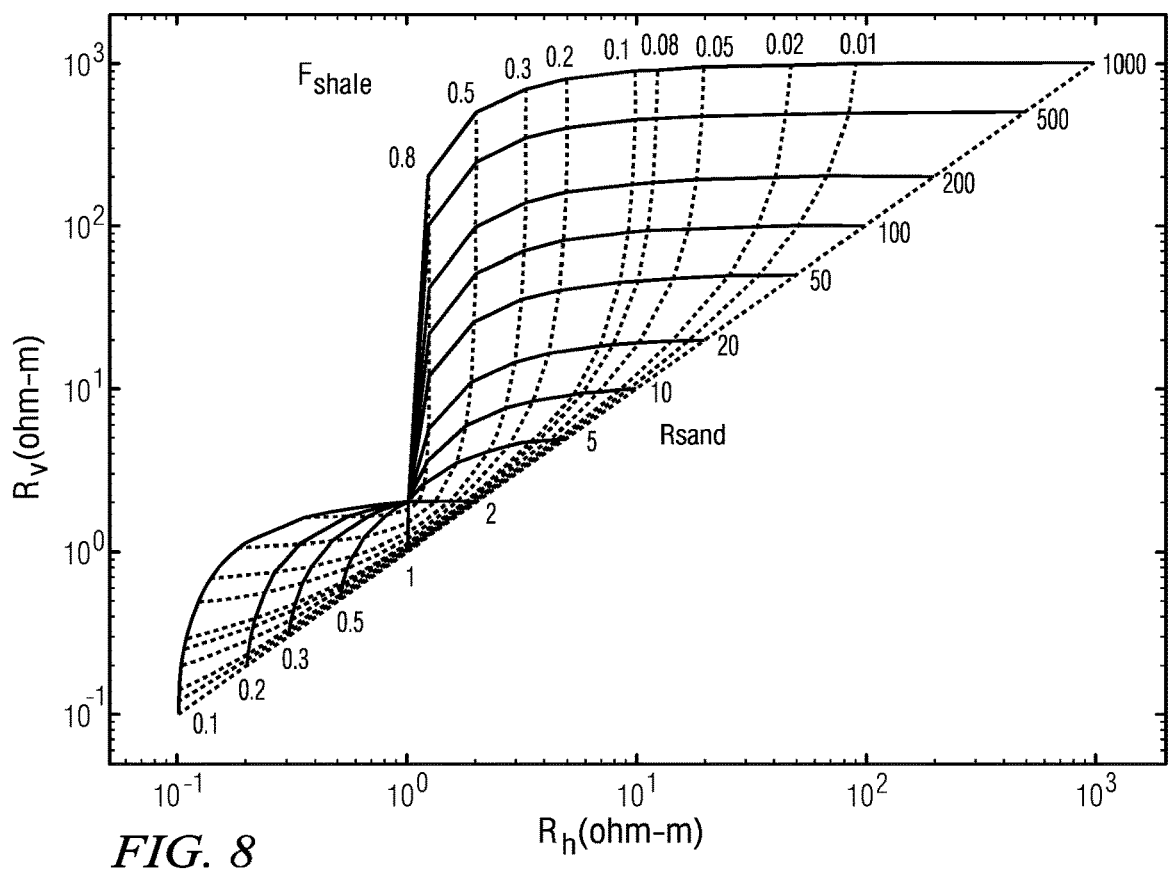
FIG. 7 depicts a resistivity cross-plot generated for from Equation 9.

FIG. 7 depicts a resistivity cross-plot (a plot of horizontal versus vertical resistivity commonly referred to as a Klein plot or a butterfly plot) used to estimate $R_{sand}$ and $V_{shale}$ ($F_{shale}$) from full tensor electromagnetic measurements not employing multi-frequency measurements. The depicted plot was generated from Equation 9 for a representative anisotropic shale without dielectric permittivity considerations (i.e., for $\varepsilon=0$). In particular, in the depicted plot the representative shale was taken to have resistivity values of $R_{shale\_v}=0.5$ S/m and $R_{shale\_h}=1.0$ S/m. These assumed values may be obtained, for example, from previous measurements or other considerations. Thus the depicted cross-plot enables measurements of the vertical and horizontal resistivity of the layered formation (obtained for example via full tensor electromagnetic measurements) may be graphically transformed to values of $R_{sand}$ and $V_{shale}$ ($F_{shale}$) for any values of $R_{shale\_v}$ and $R_{shale\_h}$.

Figure 8:
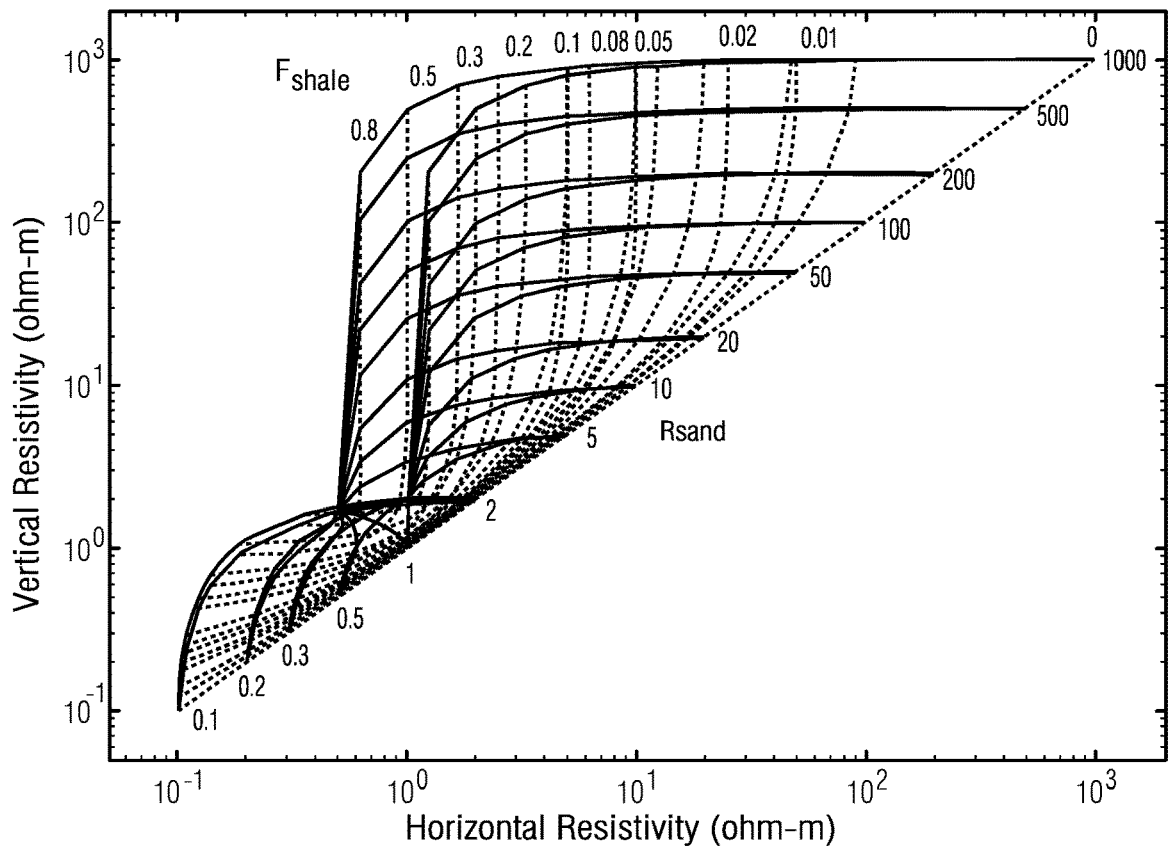
FIG. 8 depicts a resistivity cross-plot generated from the real components of Equation 12.

FIG. 8 depicts a resistivity cross-plot for inductive full tensor, complex conductivity electromagnetic measurements that account for the influence of the dielectric permittivity on the complex conductivity measurements. The depicted plot was generated from the real components of Equation 12 for a representative anisotropic shale having a non-zero dielectric permittivity. In particular, in the depicted plot, the representative shale was taken to have resistivity values of $R_{shale\_v}=0.5-0.2i$ S/m and $R_{shale\_h}=1.0-i$ S/m. FIG. 8 also depicts the cross-plot depicted on FIG. 7 for comparison purposes (in dotted lines). Note that the basic shape of the cross-plot remains the same, but that the effect of the non-zero dielectric permittivity stretches the plotted values to the left for any given values of $R_{sand}$ and $F_{shale}$ towards lower values of $R_h$. Correspondingly, values of $R_v$ and $R_h$ (obtained from the multi-frequency, full tensor electromagnetic measurements) generally yield different values for $R_{sand}$ and $F_{shale}$ when graphically transformed.

Figure 9:
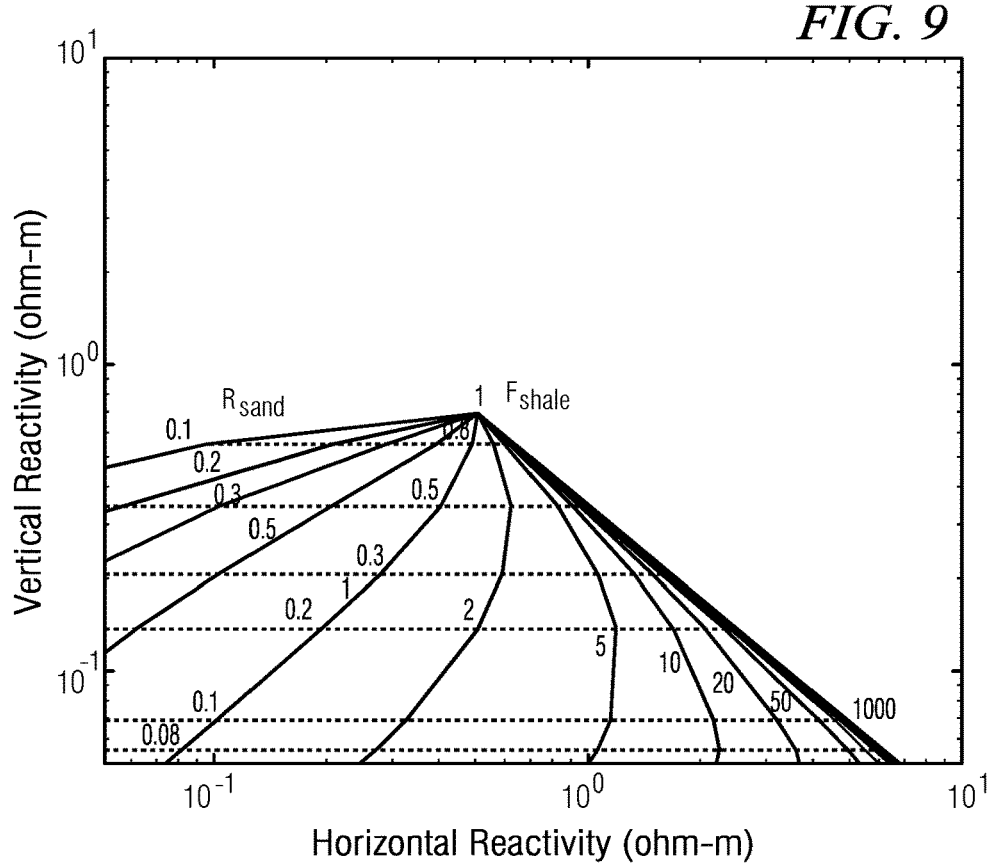
FIG. 9 depicts a resistivity cross-plot generated from the imaginary components of Equation 12.

FIG. 9 depicts a reactivity cross-plot (plotting the vertical reactivity versus the horizontal reactivity) for inductive full tensor, complex conductivity electromagnetic measurements that account for the influence of the dielectric permittivity on the complex conductivity measurements. The depicted plot was generated from the imaginary components of Equation 12 for a representative anisotropic shale having a non-zero dielectric permittivity. As in FIG. 8, the representative shale was taken to have resistivity values of $R_{shale\_v}$=0.5−0.2i S/m and $R_{shale\_h}$=1.0−i S/m. In the depicted embodiment, the vertical and horizontal reactivity (which is related to the dielectric permittivity) obtained from the multi-frequency, full tensor electromagnetic measurements may be graphically transformed to values of $R_{sand}$ and $V_{shale}$ ($F_{shale}$).

Tool and Formation Modeling

A numerical forward model of embodiments of the disclosed multi-frequency, full tensor electromagnetic measurement tool (e.g., as depicted on FIGS. 1A, 1B, and 2) may be useful in estimating petrophysical properties and electrical properties of whole core samples from the measured complex conductivity tensor of the sample. A COMSOL-based finite-element (FE) forward model and a MATLAB-based semi-analytic (SA) forward model of the electromagnetic measurement tool response were used for modeling purposes. The SA method was developed to compute the tool response modeling significantly faster than possible using the FE forward model. Both SA and FE forward models were used to quantify the helical and saddle-type coil responses in during electromagnetic induction in a frequency range from 1 to 200 kHz and electromagnetic propagation in a frequency range from 0.4 to 2 MHz.

Figure 10:
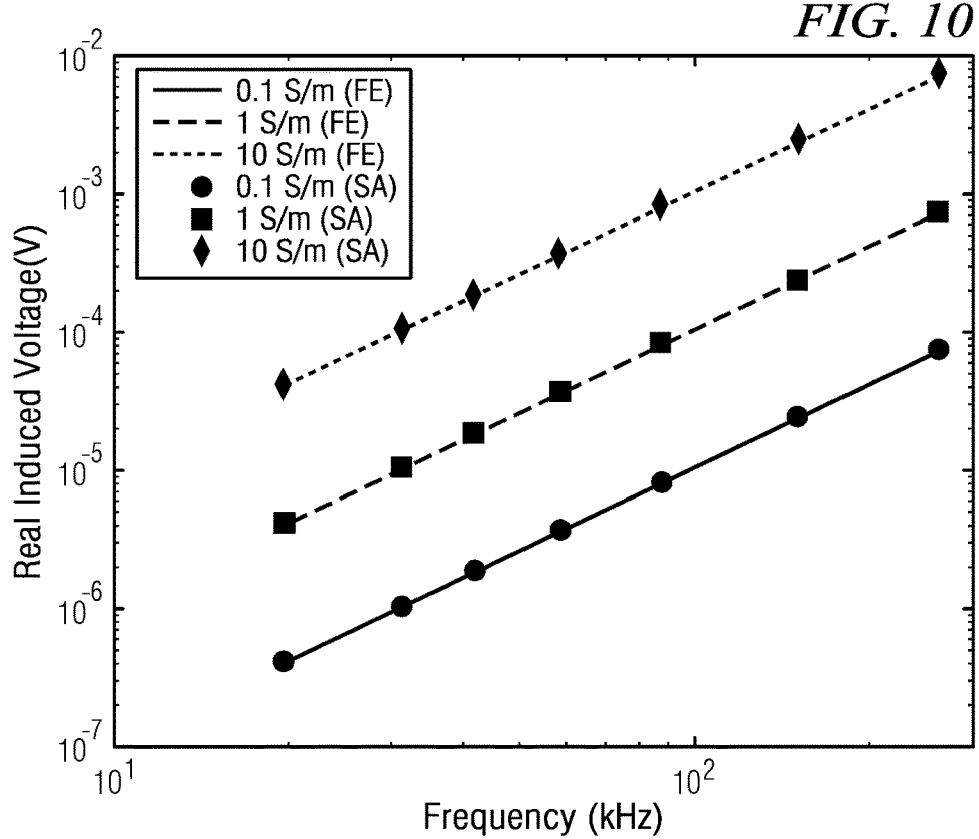
FIG. 10 depicts a log-log plot of the real induced voltage versus frequency for comparing semi-analytic model predictions against the finite element FE model predictions.

FIG. 10 depicts a log-log plot of the real induced voltage versus frequency to compare the SA model predictions against the FE model predictions for a zz coupling to three isotropic cylindrical volumes having a horizontal conductivity of 0.1, 1, and 10 S/m at frequencies of 19.6, 31.2, 41.5, 58.5, 87.6, 150.4, and 261 kHz. Good agreement was obtained between the SA and FE model predictions.

Figure 11A:
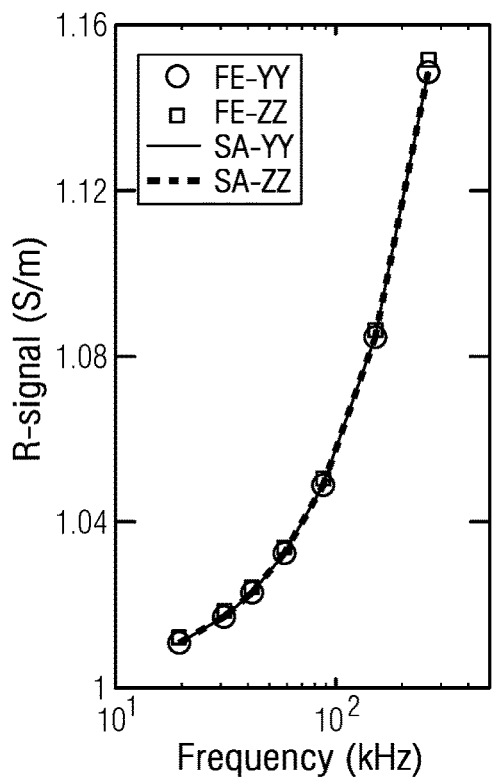
FIGS. 11A and 11B depict plots of the real and imaginary modeled signal responses of yy and zz couplings versus frequency for an isotropic volume.
Figure 11B:
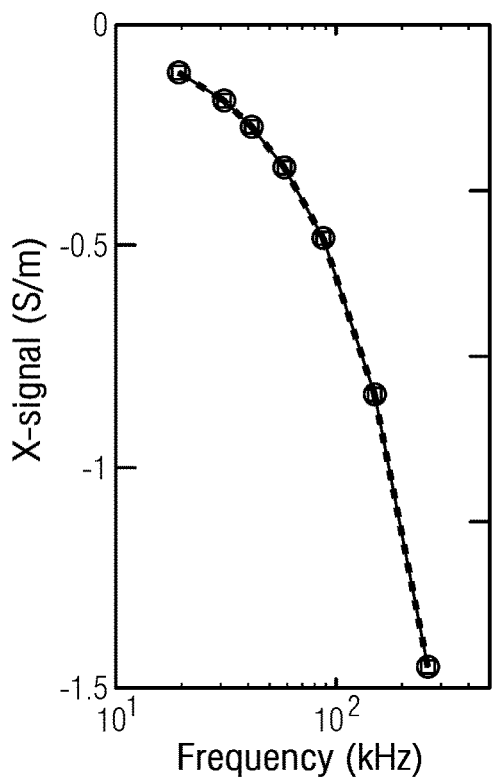

FIGS. 11A and 11B depict plots of the real and imaginary signal responses of yy and zz couplings versus frequency for an isotropic cylindrical volume having $\sigma_h$=1 S/m, $\varepsilon_r$=10⁵, and a dielectric loss factor δ=0.1 at frequencies of 19.6, 31.2, 41.5, 58.5, 87.6, 150.4, and 261 kHz. The SA model predictions closely match the FE model predictions for both the yy and zz coupling responses.

Figure 12A:
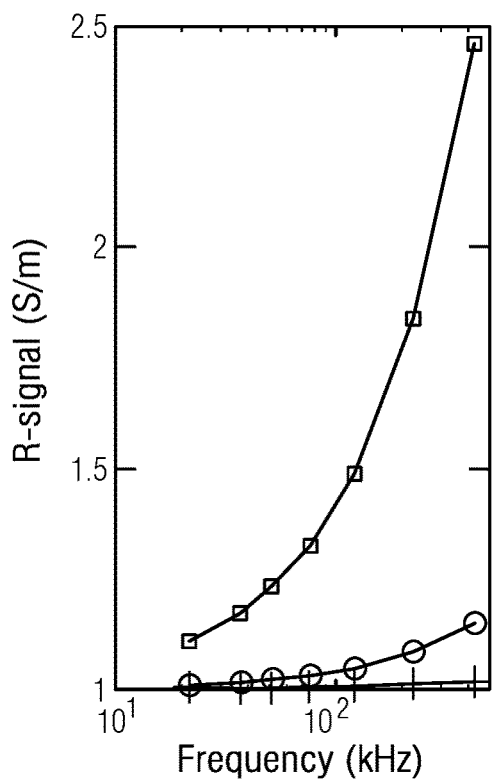
FIGS. 12A and 12B depict plots of the real and imaginary modeled signal responses of the zz coupling versus frequency for a cylindrical volume having $\sigma_h=1$ S/m, $\varepsilon_{r,h}=10^5$, $\lambda_c=\lambda_p=1$ at various values of $\delta$.
Figure 12B:
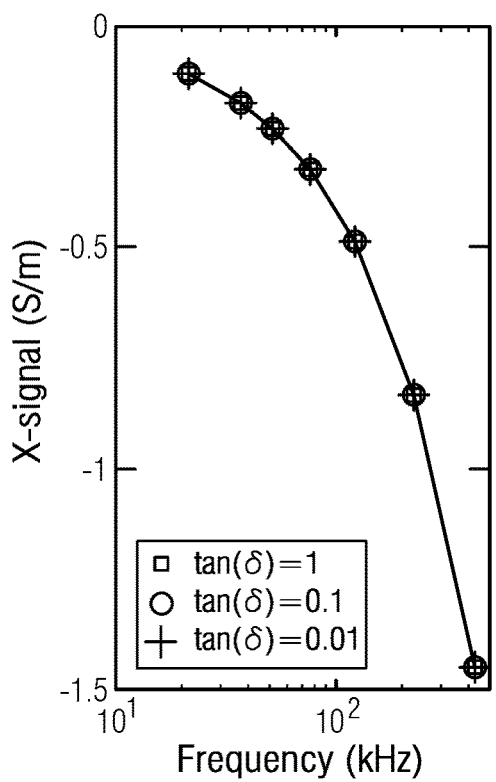

FIGS. 12A and 12B depict plots of the real and imaginary signal responses of the zz coupling versus frequency for a cylindrical volume having $\sigma_h$=1 S/m, $\varepsilon_{r,h}$=10⁵, $\lambda_c$=$\lambda_p$=1 at various values of δ (where $\lambda_c$ represents a conductivity anisotropy ratio and $\lambda_p$ represents a permittivity anisotropy ratio). As depicted the dielectric loss factor δ has negligible effect on the imaginary signal response. However, the real signal response is influenced significantly by variation in δ. A cylindrical volume having a δ of 1 exhibits more than 50% increase in the real signal response compared to that of sample having negligible δ at 58.5 kHz. The effect of δ is also observed to increase with frequency, resulting in more than 200% increase at 261 kHz. Since only the real signal response of the modeled electromagnetic tool is observed to be sensitive to variation in δ accurate resistivity interpretation of the real signal response to a whole core sample of large permittivity may account for the effect of variation in the dielectric loss factor.

Interfacial polarization is a frequency dispersive phenomena that may lead to frequency dispersion of effective conductivity and permittivity of geomaterials. Understanding the complex conductivity behavior as a function of frequency may enable the real part of the resistivity to be corrected for the dispersion effects (which otherwise might be interpreted as a change of the formation resistivity due to the presence or lack of hydrocarbons). The Cole-Cole empirical model is widely used in the industry to interpret dielectric dispersion measurements of geomaterials. However, there is no direct relationship between the parameters of the Cole-Cole model and petrophysical properties. The Cole-Cole model may be expressed as follows:

$$\varepsilon_r^* = \varepsilon_{r,\infty} + \frac{\varepsilon_{r,s} - \varepsilon_{r,\infty}}{1 + (i\omega\tau)^{(1-\alpha)}} \quad (14)$$

where $\varepsilon_r^*$ represents the frequency dependent complex relative permittivity, $\varepsilon_{r,\infty}$ represents the relative dielectric permittivity at high frequency (~GHz), $\varepsilon_{r,s}$ represents the relative dielectric permittivity at low frequency (~mHz), ω represents operating angular frequency (s⁻¹), and τ is time constant (s), and (1−α) represents the frequency dispersion parameter.

The SA model was used to predict the real and imaginary signal responses to a cylindrical volume having of $\sigma_h$=1 S/m and $\lambda_c$=$\lambda_p$=1 for various values of the Cole-Cole parameters, namely, τ, α, and $\varepsilon_{r,s}$−$\varepsilon_{r,\infty}$, that describe the dielectric dispersion characteristics of the cylindrical volume. As indicated below, it was observed that the real signal response was highly sensitive to variation in the Cole-Cole parameters. It may be advantageous in making accurate resistivity interpretation of samples exhibiting dielectric dispersion to interpret both the real and imaginary signal responses by coupling the Cole-Cole empirical model with the forward model of the electromagnetic measurement tool (e.g., in this case using the SA model).

Figure 13A:
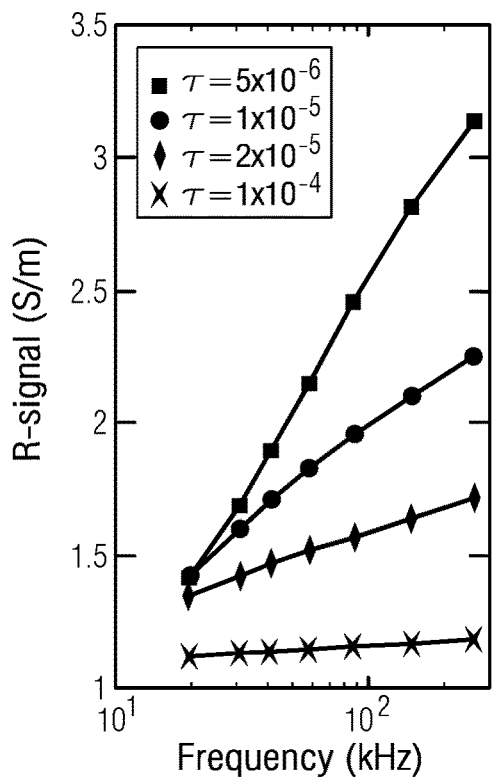
FIGS. 13A and 13B plot the real and imaginary modeled signal responses of the zz coupling to an isotropic cylindrical volume having $\sigma_h=1$ S/m, $\lambda_c=\lambda_p=1$, $\varepsilon_{r,s}=10^6$, and $\alpha=0.15$ for various values of $\tau(s)$.
Figure 13B:
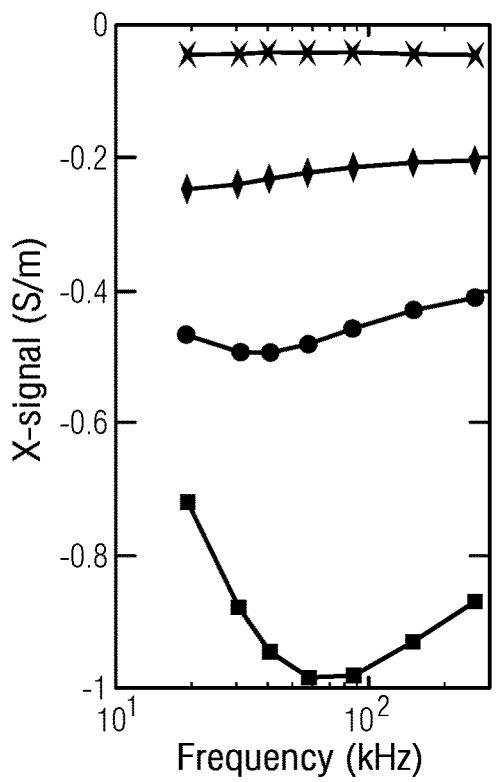

FIGS. 13A and 13B plot the real and imaginary signal responses of the zz coupling to an isotropic cylindrical volume having $\sigma_h$=1 S/m, $\lambda_c$=$\lambda_p$=1, $\varepsilon_{r,s}$=10⁶, and α=0.15 for various values of τ(s). Note that the peak of the imaginary signal response, corresponding to the loss of complete polarization, shifts to lower frequencies with an increase in τ. Note also, that both real and imaginary signal responses increase with decreasing τ, which generally correlates to a decrease in the size of inclusions. Substantial increases in both the real and imaginary signal responses occur for samples of τ smaller than 2×10⁻⁵ s. The modeling results depicted on FIG. 7 further indicate that the real and imaginary signal responses approach those of uncontaminated sample that are free from effects of dielectric permittivity and dielectric dispersion for samples having τ greater than 10⁻⁴ s.

Figure 14A:
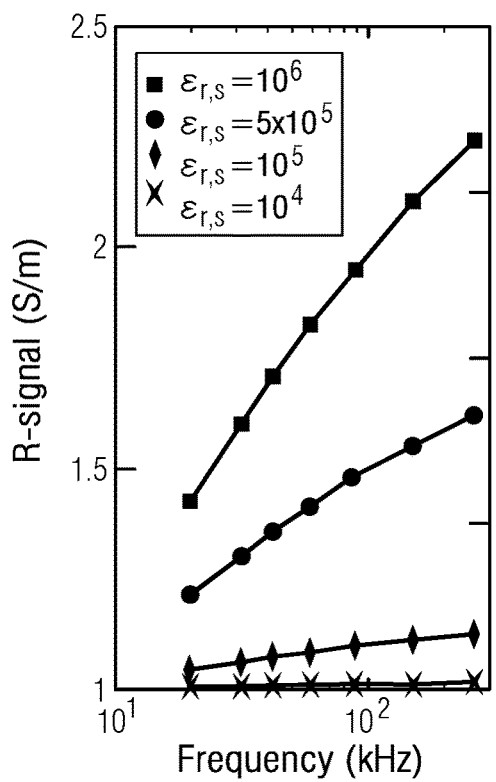
FIGS. 14A and 14B plot the real and imaginary modeled signal responses of the zz coupling to an isotropic cylindrical volume having $\sigma_h=1$ S/m, $\lambda_c=\lambda_p=1$, $\tau=10^{-5}$ sec, and $\alpha=0.15$ for various values of $\varepsilon_{r,s}$.
Figure 14B:
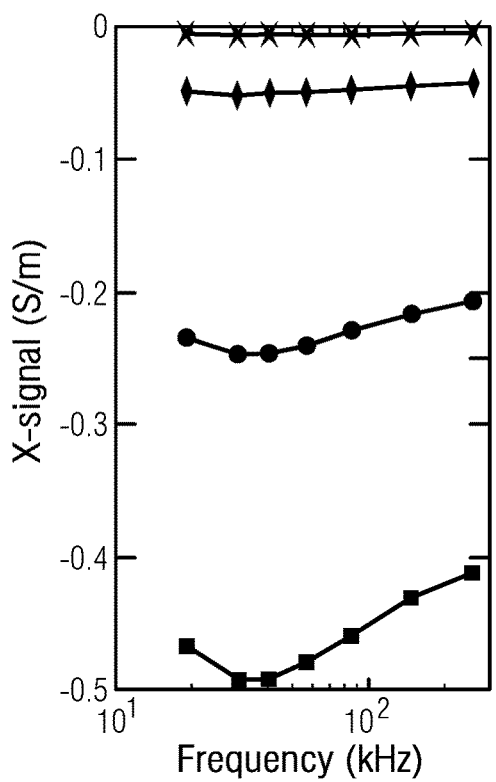

FIGS. 14A and 14B plot the real and imaginary signal responses of the zz coupling to an isotropic cylindrical volume having $\sigma_h$=1 S/m, $\lambda_c$=$\lambda_p$=1, τ=10⁻⁵ sec, and α=0.15 for various values of $\varepsilon_{r,s}$. Note that significant increase in the real and imaginary signal responses is observed only occurs only for $\varepsilon_{r,s}$ greater than 10⁵. It is believed that the frequency dispersion in the real and imaginary signal responses increases with the increase in $\varepsilon_{r,s}$ due to greater storage of charges.

Figure 15A:
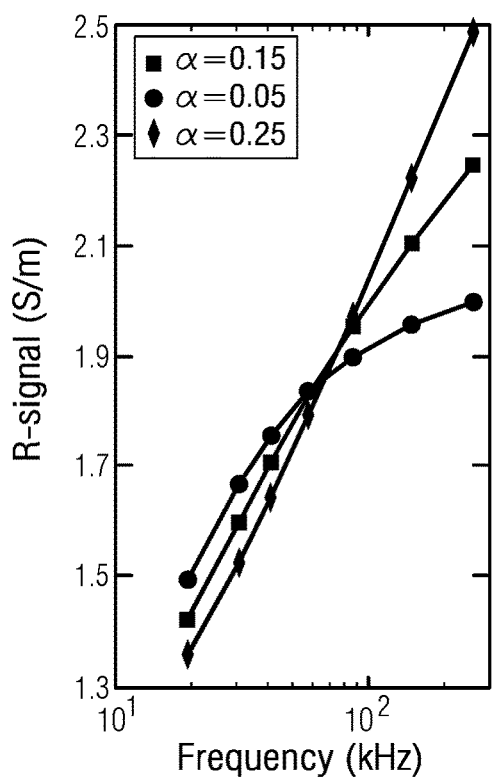
FIGS. 15A and 15B SA plot the real and imaginary modeled signal responses of the zz coupling to an isotropic cylindrical volume having $\sigma_h=1$ S/m, $\lambda_c=\lambda_p=1$, $\tau=10^{-5}$ sec, and $\varepsilon_{r,s}=10^6$ for various values of $\alpha$.
Figure 15B:
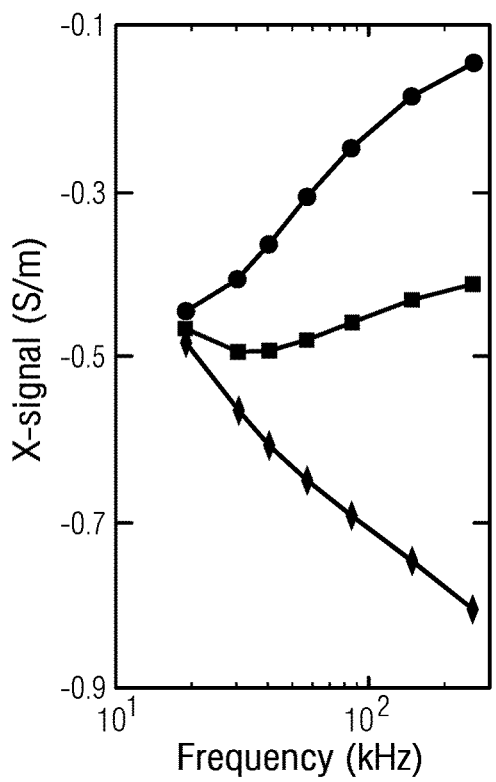

FIGS. 15A and 15B SA plot the real and imaginary signal responses of the zz coupling to an isotropic cylindrical volume having $\sigma_h$=1 S/m, $\lambda_c$=$\lambda_p$=1, τ=10⁻⁵ sec, and $\varepsilon_{r,s}$=10⁶ for various values of α. A decrease in α, which tends to correspond to an increase in the homogeneity of the core sample, reduces the real and imaginary signal responses (likely due to a reduction of surfaces producing interfacial polarization). Interestingly, a sample having α=0.05 exhibits a frequency dispersion of the imaginary signal response that reduces the response with increasing frequency, while a sample of α=0.25 exhibits a frequency dispersion of the imaginary signal response that increases the response with increasing frequency. In other words, the peak of the imaginary signal response shifts to higher frequencies with an increase in a that honors the effect of increase in heterogeneity of the sample. This relationship of the imaginary signal response to a may be advantageously used to quantify the degree of heterogeneity in a formation core.

Figure 16A:
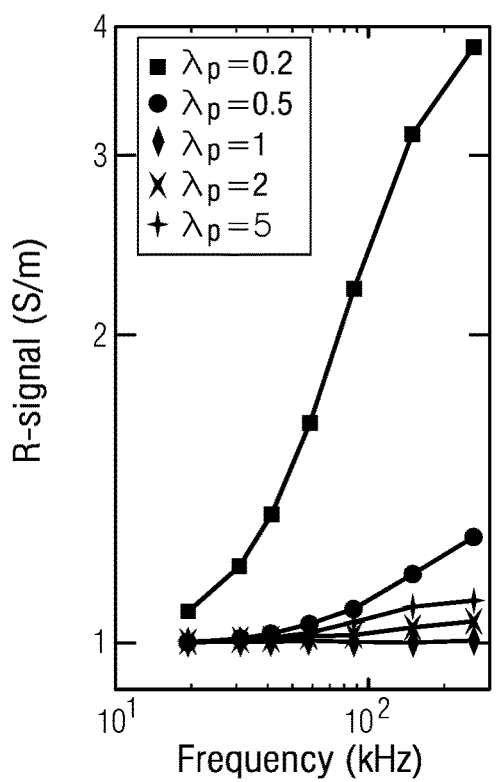
FIGS. 16A and 16B plot the real and imaginary modeled signal responses of the yy coupling to an isotropic cylindrical volume having $\sigma_h=1$ S/m, $\lambda_c=1$, and $\varepsilon_{r,s}=10^5$, for various values of $\lambda_p$.
Figure 16B:
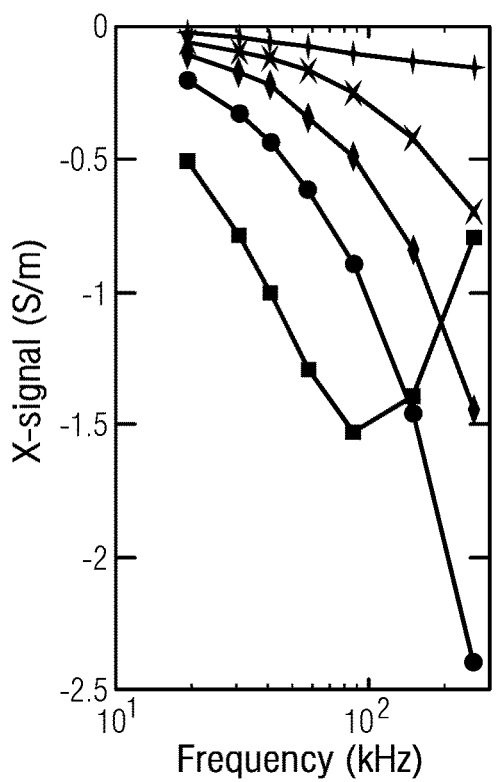

FIGS. 16A and 16B plot the real and imaginary signal responses of the yy coupling to an isotropic cylindrical volume having $\sigma_h$=1 S/m, $\lambda_c$=1, and $\varepsilon_{r,s}$=10$^5$, for various values of $\lambda_p$. FE model predictions indicate that whole core samples having of $\varepsilon_r$>10$^4$ produce substantial negative imaginary signal response. However, such large values of $\varepsilon_r$ do not generally affect the real signal response since it is the dielectric loss factor and the frequency dispersive behavior of a that generally give rise to significant changes in the real signal response. For example, in FIG. 16A the blue curve indicates that the real signal response is close to 1 S/m and is not affected by the large $\varepsilon_{r,h}$ of the sample. However, the blue curve in FIG. 16B, shows that the imaginary signal response exhibits large negative, frequency-dispersive values in the electromagnetic induction frequency range. With reference back to FIGS. 12A and 12B, the real signal response was observed to be significantly affected by the dielectric loss factor of the whole core sample.

Experimental Measurements

Various synthetic samples were prepared using glass bead packs in cylindrical glass vases having the following dimensions: 2 foot long, 4 inch outer diameter, 3.8 inch inner diameter. An inclusion-free glass-bead pack was prepared by filling the glass vase with glass beads having a radius of 575 μm and then fully saturating the pore spaces between the glass beads a brine having a conductivity of 3.75 S/m. The glass beads were Megalux beads manufactured by Swarco Company (http://www.swarco.com/en/Products-Service/Traffic-Materials/Glass-Beads). Inclusion containing samples were prepared as follows. A conductive-mineral-bearing pack was prepared by filling the glass vase with a mixture of the aforementioned glass beads and conductive mineral inclusions of a particular size to obtain a 2-inch thick layer. The aforementioned brine was the poured into the glass vase to fully saturate the 2-inch thick layer. The vase was then vibrated using a mechanical hand-held shaker to consolidate the mixture, remove trapped air bubbles, and uniformly distribute the pore-filling brine. These steps were repeated until the entire cylinder tightly-filled with glass beads, inclusions, and brine. The brine filled porosity of these samples was about 38%. Two different pyrite spherical inclusion sizes were utilized: (i) Pyrite Red having an average diameter of 50 μm and (ii) Pyrite Yellow having an average diameter of 130 μm. The pyrite inclusions were obtained from Washington Mills (http://www.washington-mills.com/products/iron-pyrite/). Two sizes of flaky graphite inclusions were also used: (i) #2 flake graphite having a 50×200 mesh size and an average surface area of 0.02 mm$^2$ and (ii) #1 flake graphite having a 50×80 mesh size and an average surface area of 0.06 mm$^2$. The graphite flakes were manufactured by Dixon Graphite. The samples containing inclusions were prepared with multiple volume fractions of the inclusion phase.

With reference to FIGS. 17A-23B, plots of the real and imaginary signal responses versus frequency are depicted for various of the synthetic samples prepared as described above. In these plots the measurements are identified with discrete points while SA model predictions are plotted using solid or dotted curves. The multi-frequency, triaxial electromagnetic measurements were made using the measurement tool described above with respect to FIGS. 1 and 2 at the same discrete frequencies described above with respect to FIGS. 10-16B (19.6, 31.2, 41.5, 58.5, 87.6, 150.4, and 261 kHz).

Figure 17A:
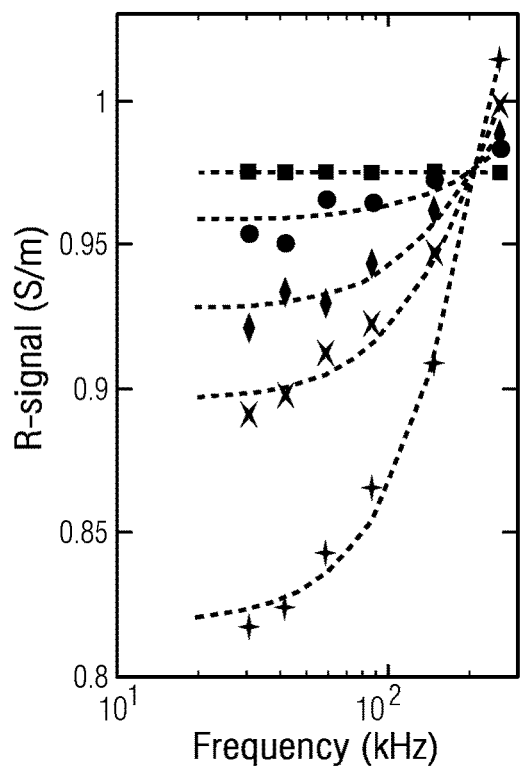
FIGS. 17A and 17B depict plots of the measured real and imaginary signal responses of a zz coupling to frequency for samples containing various volume fractions of the Pyrite Red inclusions.
Figure 17B:
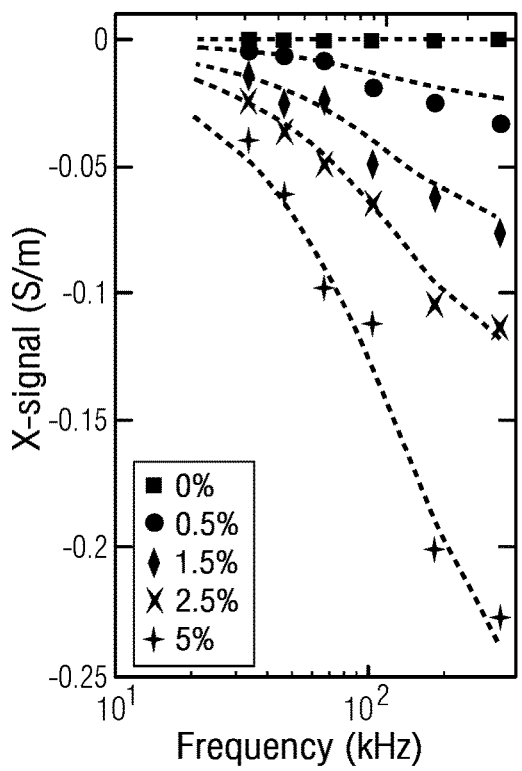
Figure 18A:
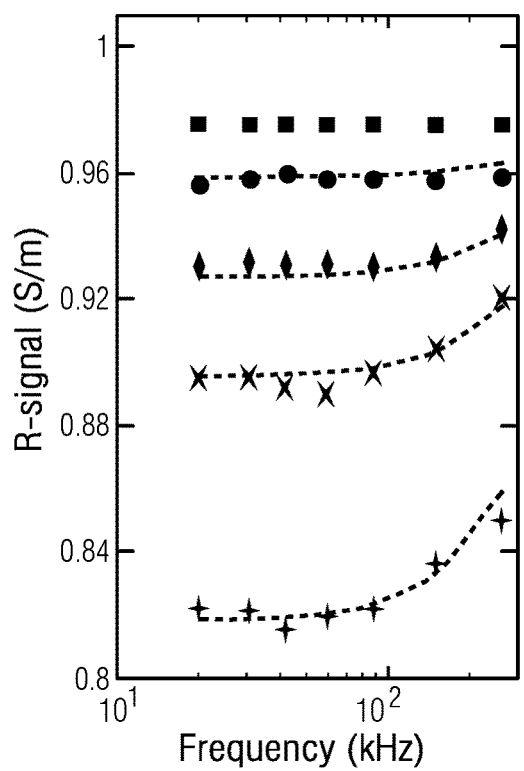
FIGS. 18A and 18B depicts plots of the measured real and imaginary signal responses of a yy coupling to frequency for the same samples as shown on FIGS. 17A and 17B.
Figure 18B:
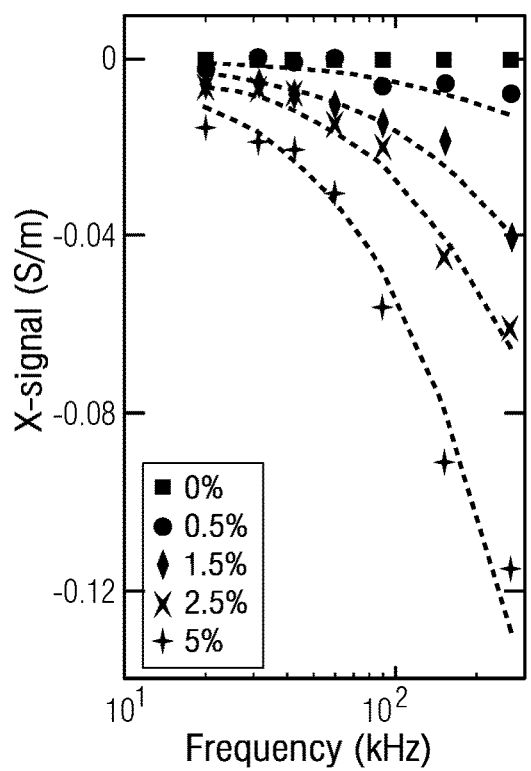

FIGS. 17A and 17B depict plots of the measured real and imaginary signal responses of a zz coupling to frequency for samples containing various volume fractions of the Pyrite Red inclusions (0, 0.5, 1.5, 2.5, and 5 volume percent). FIGS. 18A and 18B depict plots of the measured real and imaginary signal responses of a yy coupling to frequency for the same samples.

In FIGS. 17A-18B, the frequency dispersions of the real and imaginary signal responses were observed to increase with increasing volume fraction of the inclusions. This is believed to be caused by the difference between the static and high-frequency limits of effective conductivity and relative permittivity increasing with the increase in the volume content of pyrite inclusions. Large negative imaginary signal responses were measured for the pyrite-bearing glass-bead packs, further indicating that the presence of pyrite inclusions gives rise to a substantial dielectric permittivity associated with interfacial polarization phenomena. Notably, the real and imaginary signal responses obtained for the yy coupling (FIGS. 18A and 18B) are distinct from those obtained for the zz coupling (FIGS. 17A and 17B), implying that the pyrite-bearing glass-bead packs possess both conductivity and permittivity anisotropy. The real signal response mostly decreases, while the negative imaginary signal response increases in magnitude with increasing volume fraction of the inclusion phase.

Figure 19A:
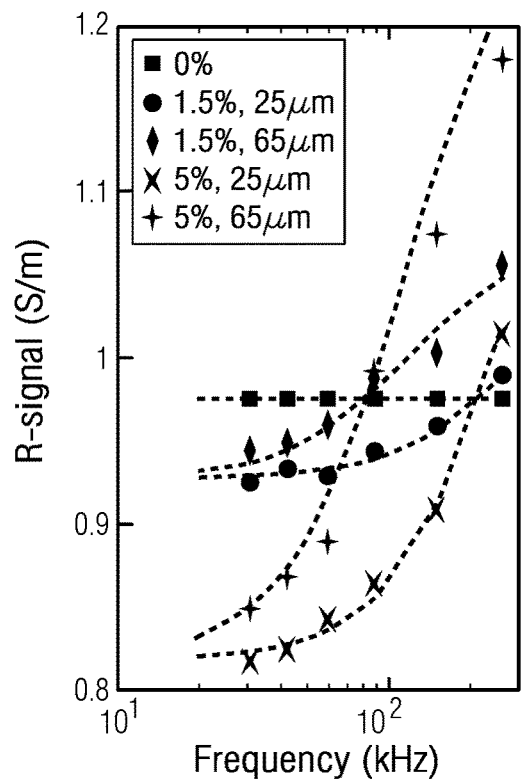
FIGS. 19A and 19B depict plots of the measured real and imaginary signal responses of a zz coupling to frequency for samples containing Pyrite Red (25 μm) or Pyrite Yellow (65 μm) inclusions for various volume fractions of the inclusion phase.
Figure 19B:
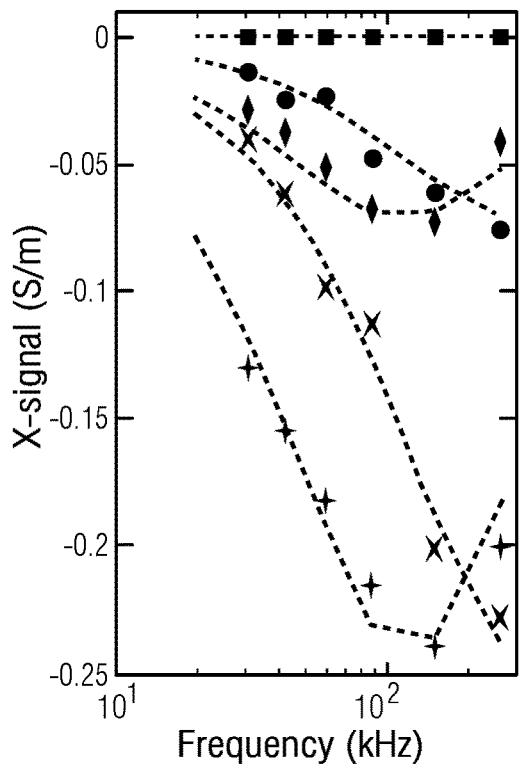

FIGS. 19A and 19B depict plots of the measured real and imaginary signal responses of a zz coupling to frequency for samples containing Pyrite Red (25 μm) or Pyrite Yellow (65 μm) inclusions for various volume fractions of the inclusion phase (0, 1.5, and 5 volume percent). The frequency dispersions of the real and imaginary signal responses were observed to increase with increasing size of pyrite inclusions, likely due to the larger-sized conductive inclusions failing to fully polarize at lower frequencies as compared to the smaller-sized conductive inclusions. The samples including the larger-diameter Pyrite Yellow inclusions exhibited a peak in the imaginary signal response (FIG. 19B). The real and imaginary signal responses generally increased with an increasing the size of inclusion. Moreover, the sensitivity of the real signal responses of the yy and zz couplings to the variations in size and volume fraction of pyrite inclusions was observed to decrease, while that of the negative imaginary signal responses of the yy and zz couplings was observed to increase in magnitude with increasing operating frequency. At an operating frequency of 58.5 kHz, the presence of 1.5 volume percent pyrite inclusions resulted in approximately 5 percent decrease in the real signal response with respect to the real signal response of an inclusion free sample and produced an imaginary signal response of approximately −25 mS/m. Furthermore, at an operating frequency of 58.5 kHz and at a volume fraction of 1.5 volume percent pyrite inclusions, a 160 percent increase in the size of the inclusions (from 25 μm to 65 μm), resulted in a 3 percent increase in the real signal response and a 50 percent increase in the magnitude of the negative imaginary signal response.

With respect to FIGS. 20A-21B, frequency-dependent horizontal and vertical effective electrical properties of the pyrite-bearing glass-bead packs were estimated. The estimates were obtained by adjusting the input values of conductivity and relative permittivity in the above described SA model to obtain the best match of the model predictions to the multi-frequency zz and yy coupling measurements.

Figure 20A:
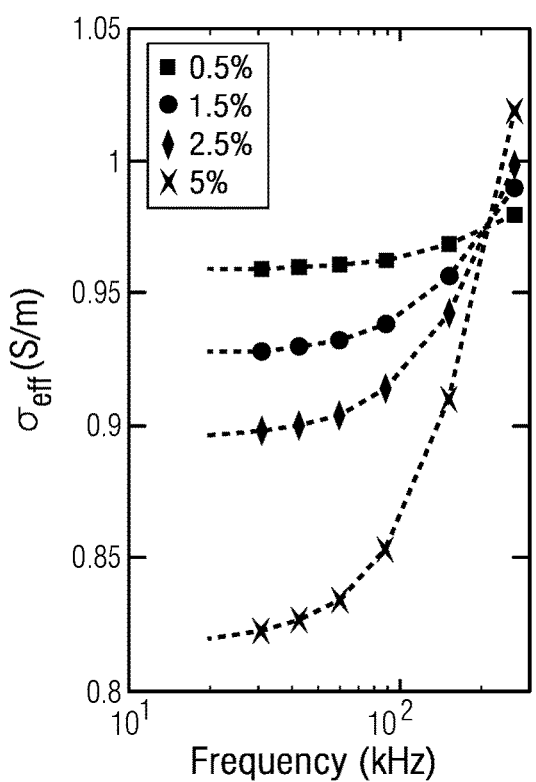
FIGS. 20A and 20B plot conductivity and relative permittivity versus frequency for samples including Pyrite Red inclusions.
Figure 20B:
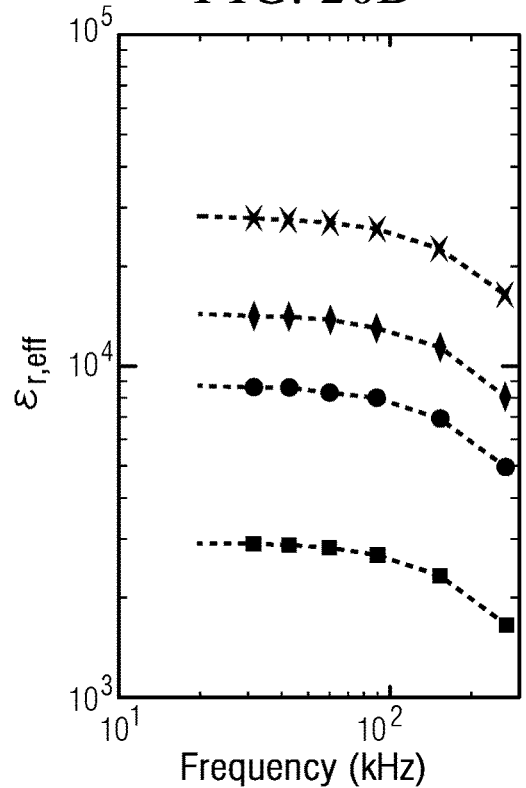

FIGS. 20A and 20B plot conductivity and relative permittivity versus frequency for the above described samples including Pyrite Red inclusions. The estimated values of the relative permittivity were on the order of (i.e., were about) $10^3$ to $10^4$. Interestingly, for low operating frequencies, the conductivity of the pyrite-bearing samples decreased with increasing volume fraction of the pyrite inclusions, possibly indicating that the pyrite inclusions act as non-conductive particles. However, at higher operating frequencies, the pyrite inclusions seem to act as conductive particles giving rise to an increase in conductivity with increasing pyrite content. This counter-intuitive conductivity behavior with respect to operating frequency may possibly be explained on the basis of perfectly-polarized interfacial polarization of pyrite inclusions due to which conductive inclusions behave as non-conductive particles at very low frequencies and as highly-conductive particles at high frequencies.

Figure 21A:
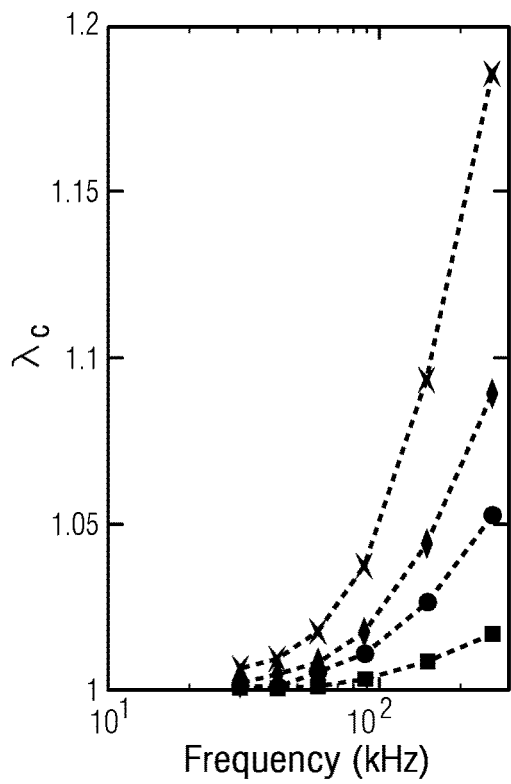
FIGS. 21A and 21B plot conductivity anisotropy and permittivity anisotropy versus frequency for same samples evaluated in FIGS. 20A and 20B.
Figure 21B:
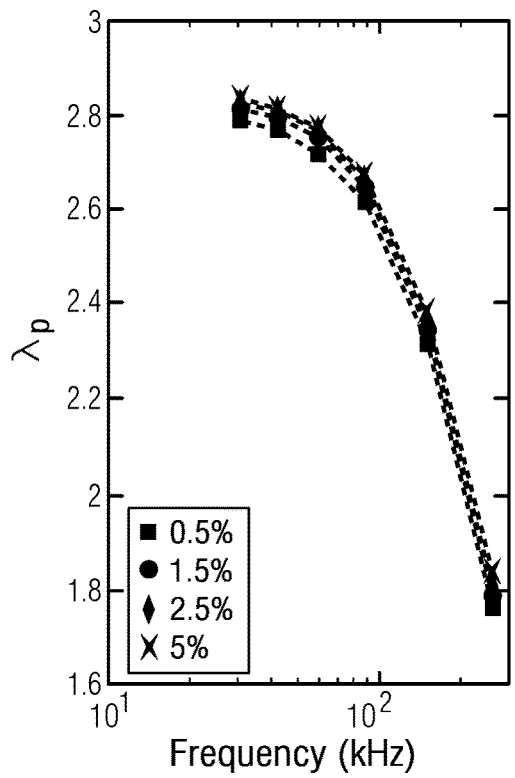

FIGS. 21A and 21B plot conductivity anisotropy and permittivity anisotropy versus frequency for same samples evaluated in FIGS. 20A and 20B. It was observed that the conductivity anisotropy $\lambda_c$ increases while the permittivity anisotropy $\lambda_p$ decreases with increasing operating frequency. These trends in $\lambda_c$ and $\lambda_p$ may be attributed to the frequency dispersion behavior of the conductivity, which was observed to increase with increasing operating frequency, and the relative permittivity, which was observed to decrease with increasing operating frequency. Furthermore, the sensitivity of $\lambda_p$ to variations in volume fraction of pyrite inclusions is negligible (FIG. 21B), while that of $\lambda_c$ strongly depends on the volume fraction (FIG. 21A). However, the frequency dependence of $\lambda_p$ (ranging from 1.7 to 2.8) was observed to be larger than that of $\lambda_c$ (ranging from 1 to 1.2).

Figure 22A:
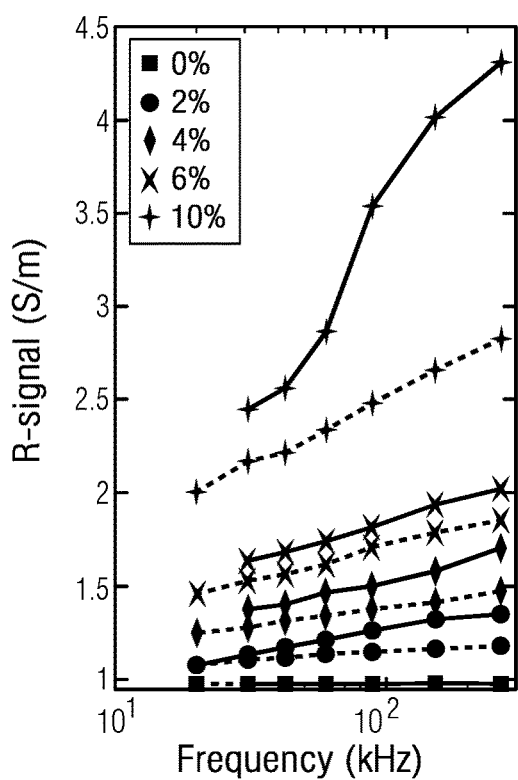
FIGS. 22A and 22B plot the real and imaginary signal responses of zz coupling (solid line) and of yy coupling (dotted line) to samples containing #2 graphite flakes for various volume fractions of graphite.
Figure 22B:
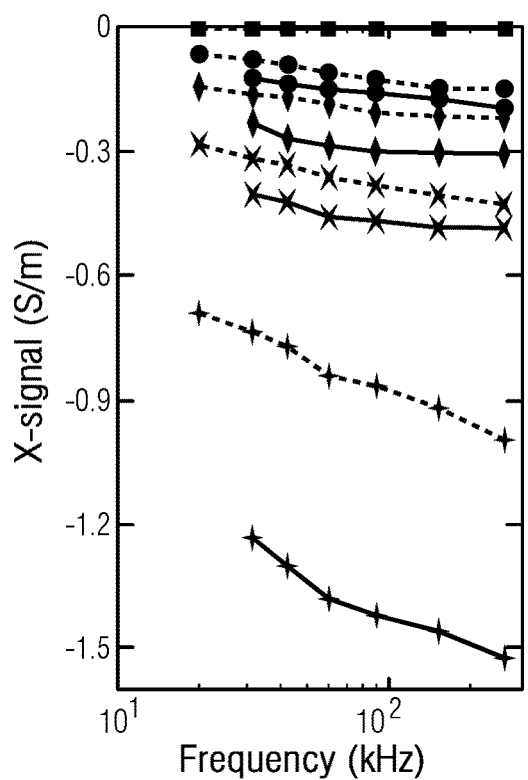

FIGS. 22A and 22B plot the real and imaginary signal responses of zz coupling (solid line) and of yy coupling (dotted line) to samples containing #2 graphite flakes for various volume fractions of the inclusion phase (at 0, 2, 4, 6, and 10 volume percent). The frequency dispersions of the real and imaginary signal responses were observed to increase with increasing volume fraction of the graphite flakes. The magnitude of the negative imaginary signal responses was much larger than that of the pyrite-bearing samples discussed above. Notably, the real and imaginary signal responses obtained for the yy coupling are distinct from those obtained for the zz coupling, possibly implying that the graphite-bearing samples possess both conductivity and permittivity anisotropy. Unlike the real and imaginary signal responses observed for the samples containing pyrite inclusions, both the real and the negative imaginary signal response was observed to increase in magnitude with increasing volume fraction of the inclusion phase. This indicates that the graphite inclusions may act as conductive particles over the electromagnetic induction frequency range. Moreover, the difference in the real signal response of samples containing pyrite inclusions versus those containing graphite inclusions highlight that the graphite inclusions tend to have higher relaxation times compared to those containing pyrite inclusions. Samples including 10 volume percent graphite were observed to exhibit large frequency-dispersive real and imaginary signal responses. However, geological rocks containing a volume fraction of graphite greater than about 4 percent are not generally considered to have productive hydrocarbon-bearing potential.

Figure 23A:
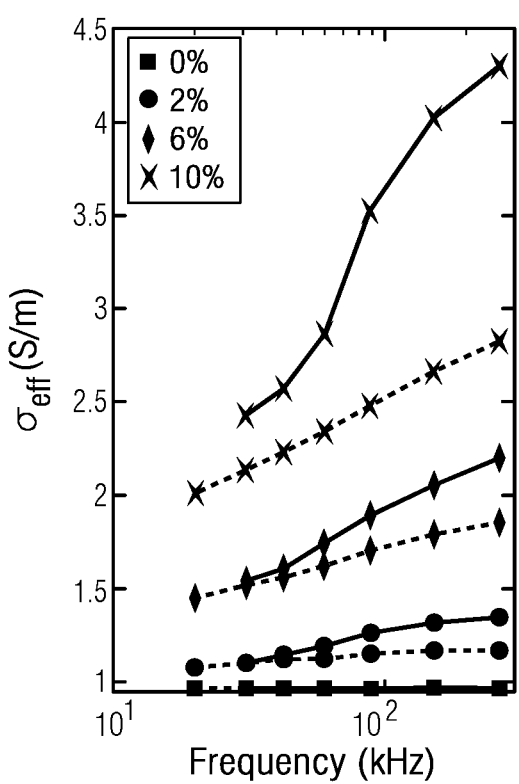
FIGS. 23A and 23B plot conductivity and relative permittivity versus frequency for the samples including #2 graphite flakes.
Figure 23B:
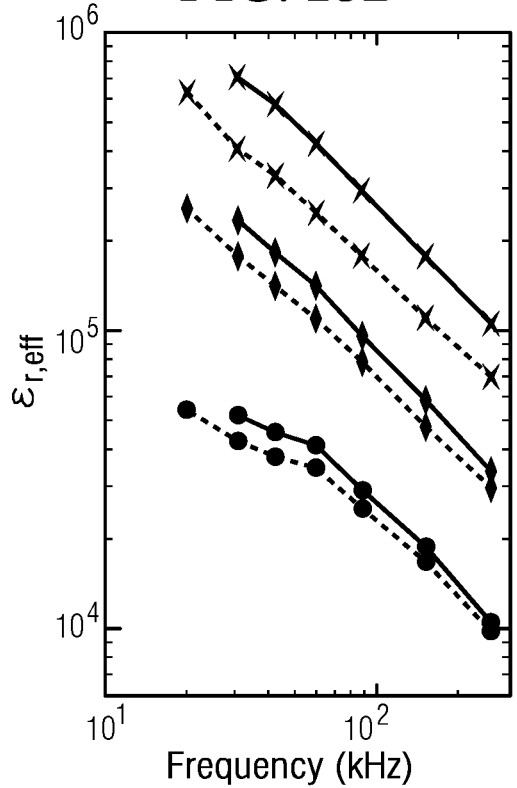

FIGS. 23A and 23B plot conductivity and relative permittivity versus frequency for the above described samples including #2 graphite flakes. The estimate conductivity and relative permittivity values were obtained by adjusting the input values of conductivity and relative permittivity in the above described SA model to obtain the best match of the model predictions to the multi-frequency zz and yy coupling measurements. The estimated values of the relative permittivity of the graphite bearing samples are in the order of about $10^4$ to about $10^6$, which are one to two orders of magnitude higher than those observed for the pyrite-bearing samples. This likely indicates that the graphite inclusions give rise to higher charge accumulation as to the pyrite inclusions (possibly due the large surface area of graphite). Owing to the higher diffusion coefficient (approximately $10^{-3}$ m$^2$s$^{-1}$) and higher conductivity ($10^5$ S/m) of graphite as compared to pyrite of ($10^{-6}$ m$^2$s$^{-1}$ and $10^3$ S/m) the relative permittivity and conductivity values of the graphite-bearing samples are larger than the corresponding pyrite-bearing samples. Moreover, a large dielectric loss factor associated with the large relative permittivity gives rise to the substantial increase in the conductivity. Furthermore, the vertical conductivity values are less dispersive than the horizontal values (similar to those of pyrite-bearing samples). However, both horizontal and vertical permittivity values have a similar magnitude of frequency dispersion and exhibit a power-law relationship with the operating frequency. Unlike the pyrite samples, the conductivity of the graphite-bearing samples increase with increasing volume fraction of graphite, possibly indicating that graphite inclusions are acting as conductive particles in the EM induction frequency range.

Various investigators have reported challenges in interpreting resistivity measurements due to the presence of conductive pyrite and graphitic-precursor inclusions in source-rock formations and shale gas reservoirs. One investigator noted a linear correlation of the total organic content (TOC) and pyrite content and suggested that resistivity measurements should be corrected for the effects of pyrite content prior to using the resistivity measurements in the delta log R method. Others have observed that both laboratory and downhole measurements in high TOC marine shale formations exhibited frequency dispersion of the 0.1 Hz to 10 kHz frequency range due to the presence of pyrite inclusions of weight fraction in the range of 1 to 5 weight percent.

In geological formations, the presence of carbon nanostructures has been found to correspond to mature zones exhibiting anomalously high electrical conductivity in well logs. It has been postulated that the occurrence of carbon nanostructures may correlate with the abundance of organic carbon, its maturity, and macroscopic electrical conductivity. Moreover, the generation of graphitic-carbon due to carbonization and/or graphitization of kerogen have been previously experimentally observed when kerogen is synthetically matured by increasing the applied temperature and pressure. Recent investigators have mentioned that a graphitic-precursor may be used for geothermometry to quantify low-grade metamorphism (330° C.). These investigators provided evidence that the graphitization of organic matter resulted in wide variety of intimately mixed conductive structures that exhibit microporous, ring, lamellar, and planar nanostructures.

Figure 24:
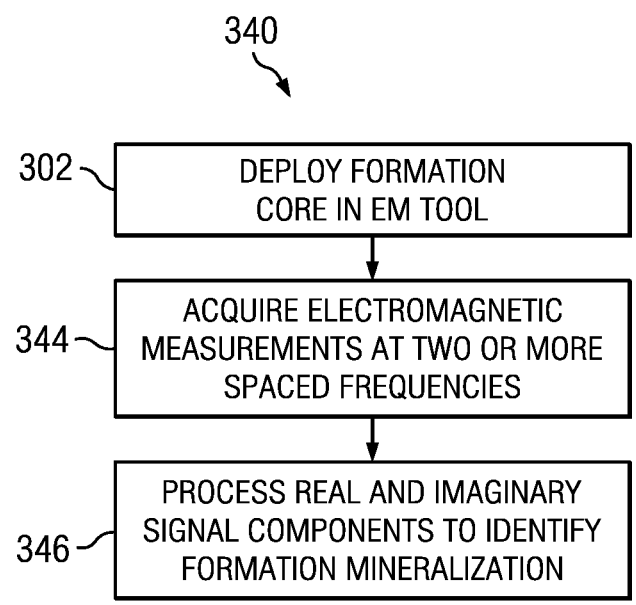
FIG. 24 depicts a flow chart of a method for discriminating the effect of graphite and pyrite mineralization on complex conductivity measurements.

FIG. 24 depicts a flow chart of a method 340 for discriminating the effect of graphite and pyrite mineralization on complex conductivity measurements and performing rock classification based on the presence of graphite and pyrite in a shale gas formation. This method is based on the distinct effects of graphite and pyrite mineralization on the multi-frequency, tri-axial, complex conductivity measurements described above. Method 340 is similar to method 300 in that it includes deploying a substantially cylindrical formation core in an electromagnetic measurement tool at 302. Triaxial electromagnetic measurements are acquired at 344 at at least two frequencies separated by over one order of magnitude (i.e., the upper frequency is 10 or more times greater than the lower frequency) and preferably by over two orders of magnitude. At 346 the real and negative imaginary signal responses of the measurements acquired at 344 may be evaluated to identify the formation mineralization to distinguish, for example, between over-mature graphite-bearing formations, mature pyrite bearing formations, and immature shale formations. The evaluation at 346 may also include processing the real and imaginary components of the relative permittivity to the weight (or volume) percent graphite in the formation (e.g., in a range from about 0 to about 6 weight percent).

Figure 25:
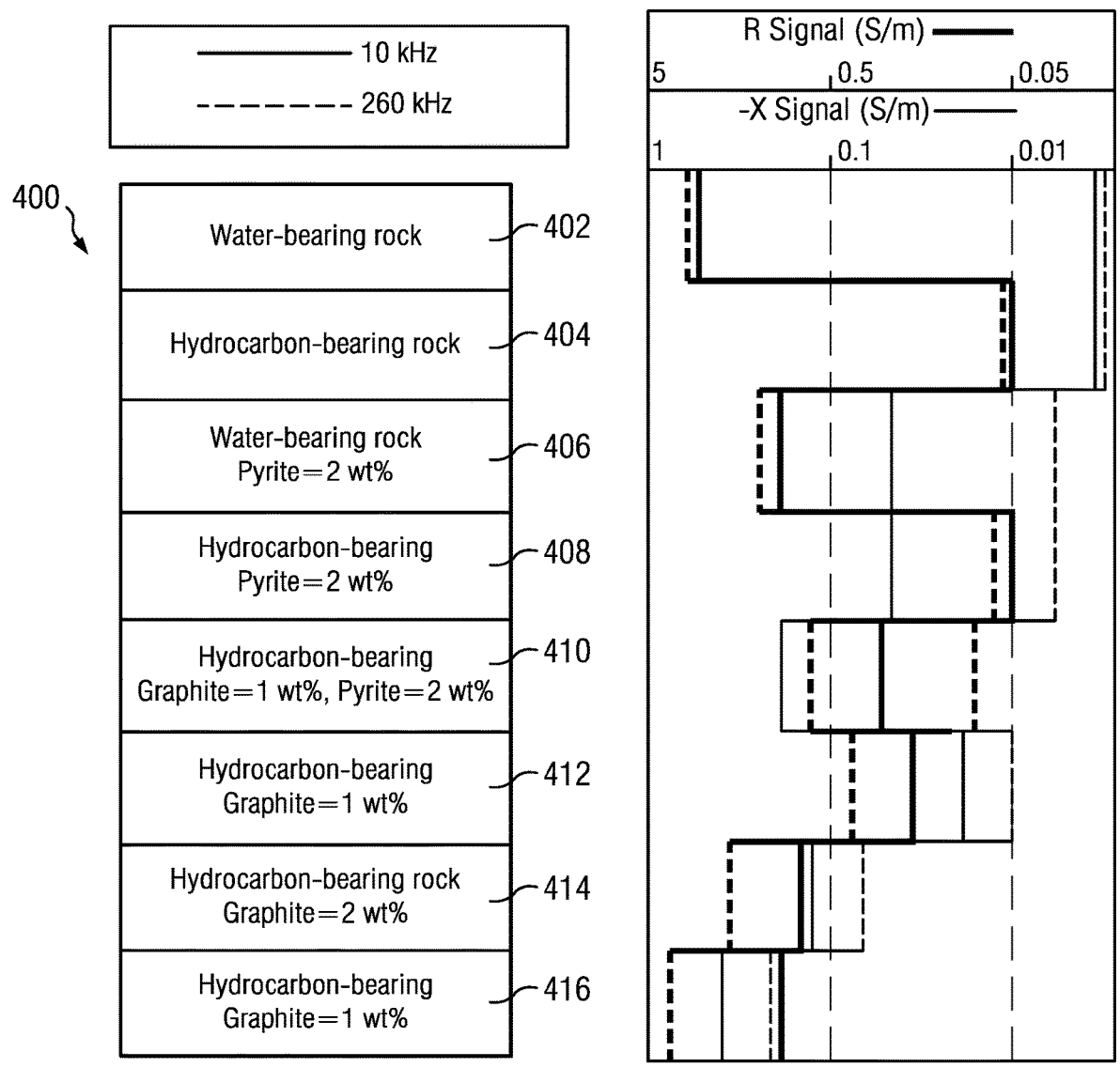
FIG. 25 depicts a quick look shale maturity interpretive chart for use with method depicted on FIG. 24.

FIG. 25 depicts a quick look shale maturity interpretive chart 400 for use with method 340 depicted on FIG. 24. Eight formation categories are classified in block form on the left-hand side of the figure. These include water bearing rock 402, hydrocarbon bearing rock 404, water bearing rock with two weight percent pyrite 406, hydrocarbon bearing rock with two weight percent pyrite 408, hydrocarbon bearing rock with one weight percent pyrite and two weight percent graphite 410, hydrocarbon bearing rock with one weight percent graphite 412, hydrocarbon bearing rock with two weight percent graphite 414, and hydrocarbon bearing rock with five weight percent graphite 416. The magnitudes of representative real and negative imaginary signal responses are depicted on the right with the dashed lines representing the higher frequency and the solid lines representing the lower frequency. By evaluating the real and imaginary signal responses in graphical (chart) form, the formation category (or categories) may be estimated.

Figure 26A:
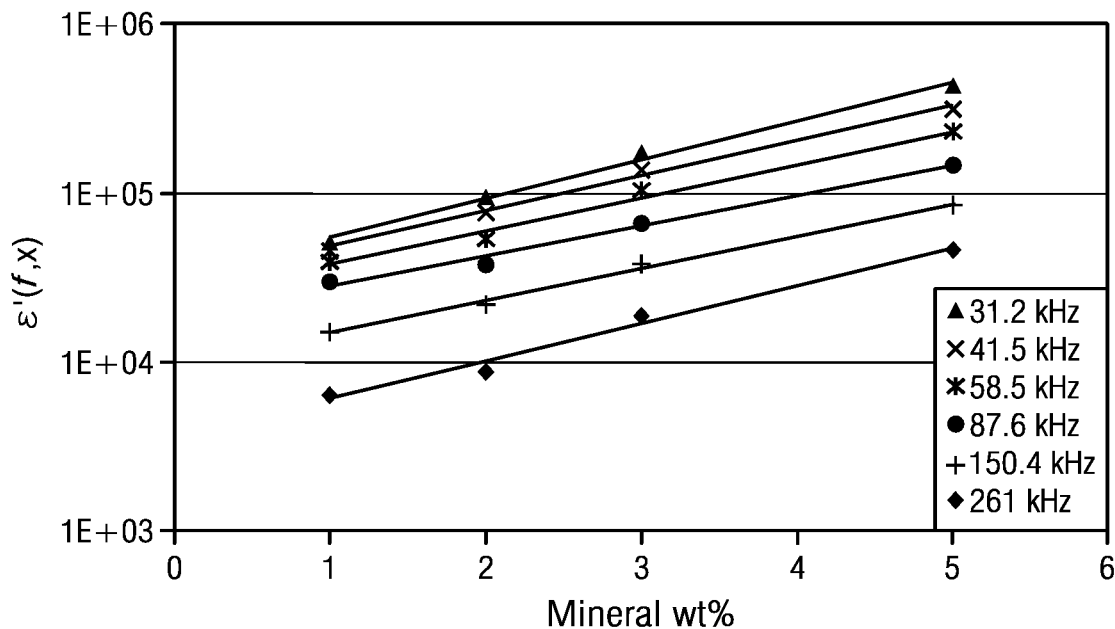
FIGS. 26A and 26B depict plots of the real and imaginary components of the relative permittivity versus weight percent graphite as a function of frequency.
Figure 26B:
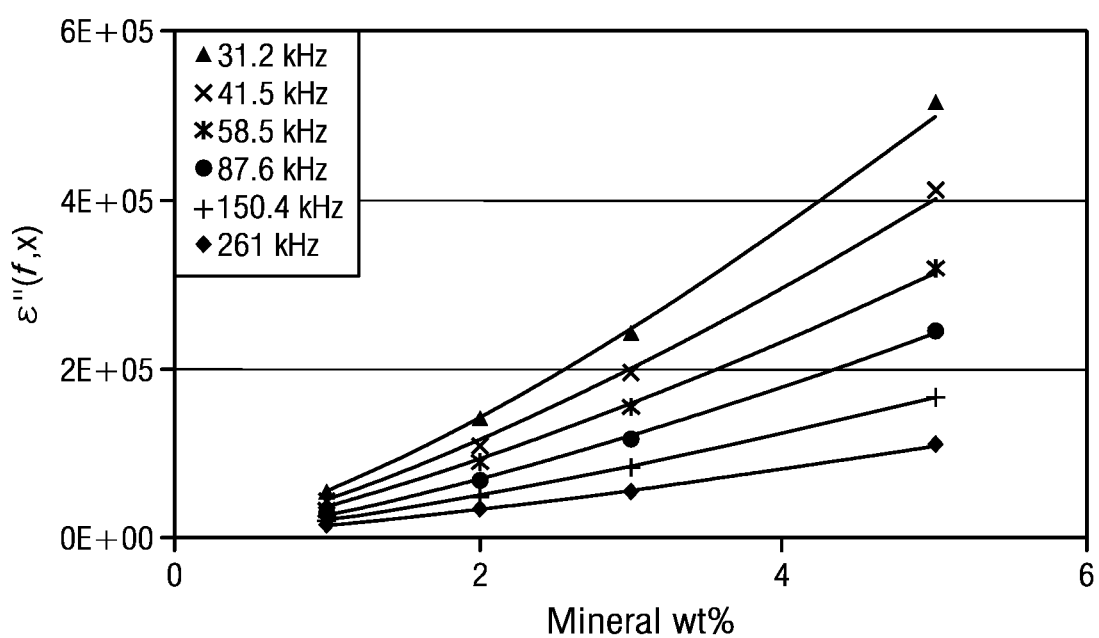

FIGS. 26A and 26B depict plots of the real and imaginary components of the relative permittivity versus weight percent graphite at six distinct frequencies. Note that in each case the relative permittivity components increase with increasing weight percent graphite in the sample. Such plots may be used to identify (e.g., graphically, numerically, and/or analytically) the weight percent graphite from the computed relative permittivity components in step 346 of method 340 (FIG. 24). The real and imaginary components of relative permittivity may be expressed mathematically as power of weight fraction and exponential of weight fraction graphite functions, for example, as follows:

$$\varepsilon'(f,x) = A(f)e^{B(f)x}$$

$$\varepsilon''(f,x) = C(f)x^{D(f)} \tag{15}$$

where A, B, C, and D represent fitting parameters, x represents the weight percent graphite, and $f$ represents the frequency of the electromagnetic wave.

Although a method and apparatus for making and processing multi-frequency triaxial electromagnetic measurements have been described in detail, it should be understood that various changes, substitutions and alternations can be made herein without departing from the spirit and scope of the disclosure as defined by the appended claims.

The invention claimed is:

1. A method for making multi-frequency electromagnetic measurements of a formation sample, the method comprising:

(a) deploying a formation sample in an electromagnetic measurement tool including a triaxial transmitter spaced apart from a triaxial receiver;
(b) causing the triaxial transmitter to transmit electromagnetic waves into the formation sample at four or more distinct and sequential frequencies;
(c) causing the triaxial receiver to receive said transmitted electromagnetic waves at each of the four or more distinct frequencies; and
(d) processing said received electromagnetic waves in combination with a formation model to compute at least one parameter of the formation model, wherein the model assumes a formation comprising alternating sand and shale layers having a spacing less than a spacing between the triaxial transmitter and the triaxial receiver, the model further including at least the following unknowns: a conductivity of the sand layers, vertical and horizontal conductivities of the shale layers, vertical and horizontal dielectric permittivities of the shale layers, and a volume fraction of the shale layers;

wherein the model is expressed mathematically as follows:

$$\frac{\sigma_v}{\sigma_v^2 + \sigma_o^2 \varepsilon_v^2} = \frac{V_{shale} \sigma_{shale\_v}}{\sigma_{shale\_v}^2 + \sigma_o^2 \varepsilon_{shale\_v}^2} + \frac{V_{sand}}{\sigma_{sand}}$$

$$\frac{i\sigma_o \varepsilon_v}{\sigma_v^2 + \sigma_o^2 \varepsilon_v^2} = \frac{V_{shale} i\sigma_o \varepsilon_{shale\_v}}{\sigma_{shale\_v}^2 + \sigma_o^2 \varepsilon_{shale\_v}^2}$$

$$\sigma_h = V_{sand} \sigma_{sand} + V_{shale} \sigma_{shale\_h}$$

$$i\sigma_o \varepsilon_h = V_{shale} i\sigma_o \varepsilon_{shale\_h})$$

wherein $\sigma_v$ and $\sigma_h$ represent vertical and horizontal conductivities of the formation, $V_{shale}$ and $V_{sand}$ represents volume fractions of the shale and sand layers, $\sigma_{sand}$ represents a conductivity of the sand layers, $\sigma_{shale\_v}$ and or $\sigma_{shale\_h}$ represent vertical and horizontal conductivities of the shale layers, $\varepsilon_{shale\_v}$ and $\varepsilon_{shale\_h}$ represent vertical and horizontal dielectric permittivities of the shale layers, and $\sigma_o = \omega \varepsilon_o$ wherein $\omega$ represents the frequency and $\varepsilon_o$ represents an absolute dielectric permittivity.

2. The method of claim 1, wherein:

(b) further comprises causing the triaxial transmitter to transmit electromagnetic energy into the formation sample at eight or more distinct and sequential frequencies; and
(c) further comprises causing the triaxial receiver to receive said transmitted electromagnetic energy each of the eight or more frequencies.

3. The method of claim 1, wherein each of the four or more frequencies is in a range from about 1 kHz to about 2 MHz.

4. The method of claim 1, wherein (d) further comprises:

(i) processing the electromagnetic waves received in (c) to compute horizontal and vertical resistivities of the formation sample;
(ii) processing real components of the model to generate a resistivity cross plot;
(iii) plotting the horizontal and vertical resistivities computed in (i) on the resistivity cross plot generated in (ii) to transform the horizontal and vertical resistivities to a resistivity of the sand layers and a volume fraction of the shale layers.

5. The method of claim 1, wherein (d) further comprises:
(i) processing the electromagnetic waves received in (c) to compute horizontal and vertical reactivities of the formation sample;
(ii) processing imaginary components of the model to generate a reactivity cross plot; and
(iii) plotting the horizontal and vertical reactivities computed in (i) on the reactivity cross plot generated in (ii) to transform the horizontal and vertical reactivities to a resistivity of the sand layers and a volume fraction of the shale layers.

6. A method for making multi-frequency electromagnetic measurements of a formation sample, the method comprising:
(a) deploying a formation sample in an electromagnetic measurement tool including a triaxial transmitter spaced apart from a triaxial receiver;
(b) causing the triaxial transmitter to transmit electromagnetic waves into the formation sample at four or more distinct and sequential frequencies;
(c) causing the triaxial receiver to receive said transmitted electromagnetic waves at each of the four or more distinct frequencies; and
(d) processing real and imaginary components of said received electromagnetic waves to identify formation mineralization.

7. The method of claim 6, wherein said identifying formation mineralization comprises discriminating between pyrite mineralization and graphite mineralization in the formation sample.

8. The method of claim 6, wherein said identifying formation mineralization comprises classifying the formation sample as being in one of the following classes: water bearing rock, hydrocarbon bearing rock, water bearing rock with about two weight percent pyrite, hydrocarbon bearing rock with about two weight percent pyrite, hydrocarbon bearing rock with about one weight percent pyrite and about two weight percent graphite, hydrocarbon bearing rock with about one weight percent graphite, hydrocarbon bearing rock with about two weight percent graphite, and hydrocarbon bearing rock with about five weight percent graphite.

9. A method for making multi-frequency electromagnetic measurements of a formation sample, the method comprising:
(a) deploying a formation sample in an electromagnetic measurement tool including a triaxial transmitter spaced apart from a triaxial receiver;
(b) causing the triaxial transmitter to transmit electromagnetic waves into the formation sample at four or more distinct and sequential frequencies;
(c) causing the triaxial receiver to receive said transmitted electromagnetic waves at each of the four or more distinct frequencies; and
(d) processing real and imaginary components of said received electromagnetic waves to identify formation mineralization, wherein said identifying formation mineralization comprises classifying the formation sample as being in one of the following classes: water bearing rock, hydrocarbon bearing rock, water bearing rock with about two weight percent pyrite, hydrocarbon bearing rock with about two weight percent pyrite, hydrocarbon bearing rock with about one weight percent pyrite and about two weight percent graphite, hydrocarbon bearing rock with about one weight percent graphite, hydrocarbon bearing rock with about two weight percent graphite, and hydrocarbon bearing rock with about five weight percent graphite.

* * * * *